US012778774B2

(12) United States Patent
Nijman et al.

(10) Patent No.: US 12,778,774 B2
(45) Date of Patent: Nov. 3, 2026

(54) MECHANICAL PROSTHETIC FOOT FOR MULTIPLE ACTIVITY LEVELS

(71) Applicant: Össur Iceland ehf, Reykjavik (IS)

(72) Inventors: Jeroen Nijman, Reykjavik (IS); Felix Starker, Reykjavik (IS); Aron Kristbjorn Albertsson, Reykjavik (IS)

(73) Assignee: Össur Iceland ehf, Reykjavik (IS)

(*) Notice: Subject to any disclaimer, the term of this patent is extended or adjusted under 35 U.S.C. 154(b) by 248 days.

(21) Appl. No.: 17/677,294

(22) Filed: Feb. 22, 2022

(65) Prior Publication Data

US 2022/0273466 A1 Sep. 1, 2022

Related U.S. Application Data

(60) Provisional application No. 63/154,519, filed on Feb. 26, 2021.

(51) Int. Cl.
*A61F 2/66* (2006.01)

(52) U.S. Cl.
CPC .......... *A61F 2/66* (2013.01); *A61F 2002/665* (2013.01); *A61F 2002/6664* (2013.01); *A61F 2002/6671* (2013.01)

(58) Field of Classification Search
CPC ...... A61F 2/60; A61F 2/66; A61F 2002/5009; A61F 2002/6614; A61F 2002/6657; A61F 2002/6671; A61F 2/76; A61F 2/6607; A61F 2002/6685
See application file for complete search history.

(56) References Cited

U.S. PATENT DOCUMENTS

| | | | | |
|---|---|---|---|---|
| 5,116,383 A | | 5/1992 | Shorter et al. | |
| 5,653,767 A | | 8/1997 | Allen et al. | |
| 6,099,572 A | | 8/2000 | Mosler et al. | |
| 6,241,776 B1 | | 6/2001 | Christensen | |
| D462,768 S | * | 9/2002 | Meyer | D24/155 |
| 6,899,737 B1 | | 5/2005 | Phillips | |

(Continued)

FOREIGN PATENT DOCUMENTS

| | | | | |
|---|---|---|---|---|
| CN | 111494070 A | | 8/2020 | |
| DE | 102014006571 B3 | * | 8/2015 | A61F 2/66 |

(Continued)

OTHER PUBLICATIONS

Petrone. Development of Instrumented Running Prosthetic Feetfor the Collection of Track Loads on Elite Athletes. Sensors (Basel). Oct. 2020; 20(20): 5758. (Year: 2020).*

(Continued)

*Primary Examiner* — Christie Bahena
(74) *Attorney, Agent, or Firm* — Knobbe, Martens, Olson & Bear, LLP

(57) ABSTRACT

A prosthetic foot can allow a user to engage in different activity levels, for example, walking and running using the same prosthetic foot. The prosthetic foot can have a generally C-shaped upper foot member coupled to a heel member near a toe portion of the prosthetic foot. The heel member can extend from a toe end to a heel end. The prosthetic foot can include a resilient member that can be split into a first component and a second component. The prosthetic foot can include a heel stiffening mechanism with different configurations to adjust a heel stiffness of the prosthetic foot.

20 Claims, 14 Drawing Sheets

(56) References Cited

U.S. PATENT DOCUMENTS

| | | | | |
|---|---|---|---|---|
| 9,017,421 | B2 | 4/2015 | Lecomte et al. | |
| 9,439,786 | B2 | 9/2016 | Nijman | |
| 10,646,357 | B2 | 5/2020 | Boiten et al. | |
| 2005/0033450 | A1* | 2/2005 | Christensen | A61F 2/66 623/53 |
| 2005/0187640 | A1 | 8/2005 | Christensen | |
| 2008/0183301 | A1 | 7/2008 | Christensen | |
| 2010/0023135 | A1 | 1/2010 | Rubie et al. | |
| 2010/0042228 | A1 | 2/2010 | Doddroe et al. | |
| 2011/0029097 | A1 | 2/2011 | Ochoa | |
| 2012/0046760 | A1* | 2/2012 | Nissels | A61F 2/66 623/55 |
| 2012/0179274 | A1 | 7/2012 | Christensen | |
| 2012/0271434 | A1 | 10/2012 | Friesen et al. | |
| 2013/0144403 | A1 | 6/2013 | Lecomte et al. | |
| 2014/0243997 | A1 | 8/2014 | Clausen et al. | |
| 2014/0277587 | A1* | 9/2014 | Colvin | A61F 2/66 623/54 |
| 2015/0282953 | A1* | 10/2015 | Smith | A61F 2/66 623/55 |
| 2015/0289996 | A1 | 10/2015 | Smith | |
| 2016/0143750 | A1* | 5/2016 | Kranner | A61F 2/66 623/55 |
| 2016/0158030 | A1 | 6/2016 | Doddroe et al. | |
| 2016/0199202 | A1 | 7/2016 | Jonasson | |
| 2016/0310298 | A1 | 10/2016 | Jonsson et al. | |
| 2018/0263793 | A1 | 9/2018 | Clausen | |
| 2019/0015224 | A1 | 1/2019 | Smith | |
| 2019/0125552 | A1 | 5/2019 | Day et al. | |
| 2020/0179138 | A1 | 6/2020 | Anderson | |
| 2021/0259857 | A1 | 8/2021 | Phillips | |
| 2022/0031477 | A1 | 2/2022 | Anderson | |
| 2022/0168117 | A1 | 6/2022 | Clausen et al. | |
| 2023/0201008 | A1 | 6/2023 | Pusch et al. | |
| 2023/0285168 | A1 | 9/2023 | Albertsson et al. | |

FOREIGN PATENT DOCUMENTS

| | | | | |
|---|---|---|---|---|
| EP | 3 131 505 | | 8/2023 | |
| FR | 3086860 | A1 * | 4/2020 | A61F 2/5046 |
| WO | WO-8905617 | A * | 6/1989 | |
| WO | WO-2013049852 | A2 * | 4/2013 | A61F 2/60 |
| WO | WO 2014/022411 | | 2/2014 | |
| WO | WO 2019/212593 | | 11/2019 | |
| WO | WO-2020022966 | A2 * | 1/2020 | A61F 2/66 |
| WO | WO 2021/178333 | | 9/2021 | |
| WO | WO 2022/180516 | | 9/2022 | |
| WO | WO 2023/170590 | | 9/2023 | |

OTHER PUBLICATIONS

International Search Report and Written Opinion in corresponding International Patent Application No. PCT/IB2022/051556, dated Jul. 25, 2022, in 22 pages.

Invitation to Pay Additional Fees in corresponding International Patent Application No. PCT/IB2022/051556, dated Jun. 2, 2022, in 15 pages.

Invitation to Pay Additional Fees in International Application No. PCT/IB2023/052173 dated Apr. 17, 2023 in 11 pages.

International Search Report and Written Opinion in International Application No. PCT/IB2023/052173 dated Jun. 7, 2023 in 18 pages.

International Preliminary Report on Patentability and Written Opinion in International Application No. PCT/IB2023/052173 dated Sep. 19, 2024 in 11 pages.

* cited by examiner

MECHANICAL PROSTHETIC FOOT FOR MULTIPLE ACTIVITY LEVELS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims the priority benefit of U.S. Provisional Application No. 63/154,519, filed Feb. 26, 2021, the entirety of which is incorporated herein by reference and should be considered a part of this specification.

BACKGROUND

Field

The present application relates to foot prostheses in general, and more particularly, to mechanical prosthetic feet configured to allow a user to engage in multiple activity levels.

Description of the Related Art

Various types of mechanical (non-powered or passive) prosthetic foot are available as substitutes for human feet and are designed to try to replicate and/or approximate the natural function of human feet. These prosthetic feet may include various components, such as foot plates and ankle modules. Some of the foot plates can have an overall shape that mimics the shape of a natural foot, with a toe region terminating at a toe end, a heel region terminating at a heel end, and a metatarsal region and an arch region between the toe region and the heel region. Some of the foot plates can curve upwardly and rearwardly (for example, generally in a C-shape or a J-shape) from the toe region and the metatarsal region to a proximal end, which can be coupled directly or indirectly to a pylon.

SUMMARY

Prosthetic feet, especially the non-powered prosthetic feet, are typically designed for a specific activity, such as walking or running. The prosthetic feet experience a different type of (for example, lower) impact during walking than during running or sports activities. During running or sports activities, the load experienced by the prosthetic foot can be up to three times a user's body weight. Current non-powered or mechanical prosthetic foot designs may not be efficient beyond the intended activity. In some instances, greater bending of the foot and/or greater push-off force at the toe may be required when a person is engaged in certain activities (such as running) than during walking or standing. On the one hand, it may not be safe or efficient to run or jog on a prosthetic foot designed for walking. Prosthetic feet designed for walking may perform poorly for running due to inadequate storage and release of energy produced during running (that is, inadequate impact absorption), and/or due to the foot being too weak to support the higher impact during running. On the other hand, running prosthetic feet can be different from walking prosthetic feet in several ways, for example, by not including a heel plate, or being set up taller than a walking foot due to the amount of compression required for running. It can be tiring or uncomfortable for a user to walk with a running prosthetic foot for daily use, for example, due to the foot members of a running foot being too stiff.

The user may need to switch to a different type of mechanical foot when engaging in different activities, for example, by wearing a prosthetic foot designed for daily use and switching to a prosthetic foot designed for running when participating in physical exercise, such as running. Moreover, the type of socket required for the different designs of the prosthetic foot may be different, making it more inconvenient to allow the user to switch between the different types of prosthetic feet for different activity levels.

It is desirable to be able to adjust the mechanical properties of one or more of regions of the prosthetic foot, for example, the heel region, based on the need of the user so that the user can use the same prosthetic foot for multiple activity levels. The multiple activity levels can include at least running and walking.

An example prosthetic foot of the present disclosure can be configured to allow a user to engage in different activity levels. The prosthetic foot can comprise a first foot member, the first foot member including a proximal end and a distal end, the proximal end configured to couple to an adapter, the first foot member including a toe region terminating at the distal end, wherein the first foot member can include a curved portion between the proximal and distal ends, and wherein a proximal portion of the first foot member between the proximal end and the curved portion can be bent toward the distal end of the first foot member; a second foot member below the first foot member when the prosthetic foot is resting on a flat surface, the second foot member including a heel end and a toe end, the heel end defining a heel end of the prosthetic foot and the toe end defining a toe end of the prosthetic foot, wherein at least a portion of the toe region of the first foot member can be coupled to the second foot member near the toe end of the second foot member; and a resilient member located between the first and second foot members, the resilient member being rearward of a coupling location of the first and second foot members.

In some embodiments, the resilient member can comprise a first component and a second component configured to be stacked together.

In some embodiments, the resilient member can comprise a plurality of grooves.

In some embodiments, the resilient member can be configured to push the prosthetic foot into plantarflexion and to provide vertical shock absorption upon heel strike.

In some embodiments, the resilient member can be configured to push the prosthetic foot into plantarflexion of up to at least 8°.

In some embodiments, the first foot member can comprise a bend at or near a metatarsal region.

In some embodiments, the first and second members can be directly coupled to each other only at the coupling location.

In some embodiments, the foot can further comprise a heel stiffening mechanism embedded in the resilient member, wherein the heel stiffening mechanism can be adjustable between at least a first configuration and a second configuration, the prosthetic foot having a first heel stiffness when the heel stiffening mechanism is in the first configuration and a second heel stiffness when the heel stiffening mechanism is in the second configuration, the first heel stiffness being different from the second heel stiffness.

In some embodiments, the heel stiffening mechanism can include a rigid core, the rigid core being generally plate-shaped having a length and a width, the length of the rigid core extending across a width of the prosthetic foot and the width of the rigid core being generally parallel to a sagittal plane of the prosthetic foot.

In some embodiments, in the first configuration, the rigid core can be generally horizontal when viewed from a lateral or medial side of the prosthetic foot.

In some embodiments, in the second configuration, the rigid core can be more vertically slanted than in the first configuration when viewed from the lateral or medial side of the prosthetic foot.

In some embodiments, the rigid core can be abutted by a resilient cushion on each side of a flat surface of the rigid core.

In some embodiments, the heel stiffening mechanism can be moved between the first and second configurations by rotating the heel stiffening mechanism about a central longitudinal axis of the heel stiffening mechanism.

In some embodiments, the heel stiffening mechanism can be the single stiffness adjustment mechanism embedded in the resilient member.

An example prosthetic foot of the present disclosure can be configured to allow a user to engage in different activity levels. The prosthetic foot can comprise a first foot member, the first foot member including a proximal end and a distal end, the proximal end configured to couple to an adapter, the first foot member including a toe region terminating at the distal end; a second foot member below the first foot member when the prosthetic foot is resting on a flat surface, the second foot member including a heel end and a toe end, the heel end defining a heel end of the prosthetic foot and the toe end defining a toe end of the prosthetic foot, wherein at least a portion of the toe region of the first foot member can be coupled to the second foot member near the toe end of the second foot member; and a resilient member located between the first and second foot members, the resilient member being rearward of a coupling location of the first and second foot members, wherein the resilient member can comprise a first component and a second component, the first and second component shaped to form pivot points to push the prosthetic foot into plantarflexion and to provide vertical shock absorption during heel strike.

In some embodiments, the toe region of the first foot member can be vertically offset from a remainder of a distal section of the first foot member.

In some embodiments, the first foot member can be generally C-shaped.

In some embodiments, the first foot member can extend forward and downward from the proximal end to the distal end.

In some embodiments, the first foot member can taper toward the distal end.

In some embodiments, the foot can further comprise a heel stiffening mechanism embedded in the resilient member, wherein the heel stiffening mechanism can be adjustable between at least a first configuration and a second configuration, the prosthetic foot having a first heel stiffness when the heel stiffening mechanism is in the first configuration and a second heel stiffness when the heel stiffening mechanism is in the second configuration, the first heel stiffness being different from the second heel stiffness.

In some embodiments, the heel stiffening mechanism can include a rigid core, the rigid core being generally plate-shaped having a length and a width, the length of the rigid core extending across a width of the prosthetic foot and the width of the rigid core being generally parallel to a sagittal plane of the prosthetic foot.

In some embodiments, in the first configuration, the rigid core can be generally horizontal when viewed from a lateral or medial side of the prosthetic foot.

In some embodiments, in the second configuration, the rigid core can be more vertically slanted than in the first configuration when viewed from the lateral or medial side of the prosthetic foot.

In some embodiments, the rigid core can be abutted by a resilient cushion on each side of a flat surface of the rigid core.

In some embodiments, the heel stiffening mechanism can be moved between the first and second configurations by rotating the heel stiffening mechanism about a central longitudinal axis of the heel stiffening mechanism.

In some embodiments, the heel stiffening mechanism can be the single stiffness adjustment mechanism embedded in the resilient member.

In some embodiments, the foot can further comprise a third foot member connected to a toe region of the first and/or second foot members.

In some embodiments, the second foot member can comprise an attachment on an upper surface of the second foot member, the attachment located at or near the toe end of the second foot member.

In some embodiments, the attachment can be configured to receive at least a portion of the toe region of the first foot member.

In some embodiments, the at least a portion of the toe region of the first foot member can be glued to the second foot member.

In some embodiments, the first and second members can be directly coupled to each other only at the coupling location.

In some embodiments, the resilient member can comprise three or more components.

An example prosthetic foot of the present disclosure can be configured to allow a user to engage in different activity levels. The prosthetic foot can comprise a first foot member, the first foot member including a proximal end and a distal end, the proximal end configured to couple to an adapter, wherein the first foot member can be curved between the proximal and distal ends; a second foot member below the first foot member when the prosthetic foot is resting on a flat surface, the second foot member including a heel end and a toe end, the heel end defining a heel end of the prosthetic foot and the toe end defining a toe end of the prosthetic foot, wherein the distal end of the first foot member can terminate proximal to the toe end of the second foot member, the first foot member coupled to the second foot member near the distal end of the first foot member; and a third foot member more anterior to the first and second foot members, a gap separating at least a portion of the first and third foot members when the foot is resting on a flat surface; wherein the prosthetic foot can include a first active area when the foot is under a lower impact and a second active area when the foot is under a higher impact, the second active area located below the first active area when the foot is resting on a flat surface, and wherein the gap can remain closed when the foot is under the higher impact.

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

DETAILED DESCRIPTION

These and other features, aspects, and advantages of the present disclosure are described with reference to the drawings of certain embodiments, which are intended to schematically illustrate certain embodiments and not to limit the disclosure.

Example Features of Mechanical Prosthetic Feet Designed for Multiple Activity and/or Impact Levels The present disclosure provides examples of a prosthetic foot allowing a user to engage in different activity levels, for example, at least walking and running. Such a prosthetic foot can include a variety of features to improve adaptability of the prosthetic foot to different activity levels (and thus different loads or impacts).

Figure 1:
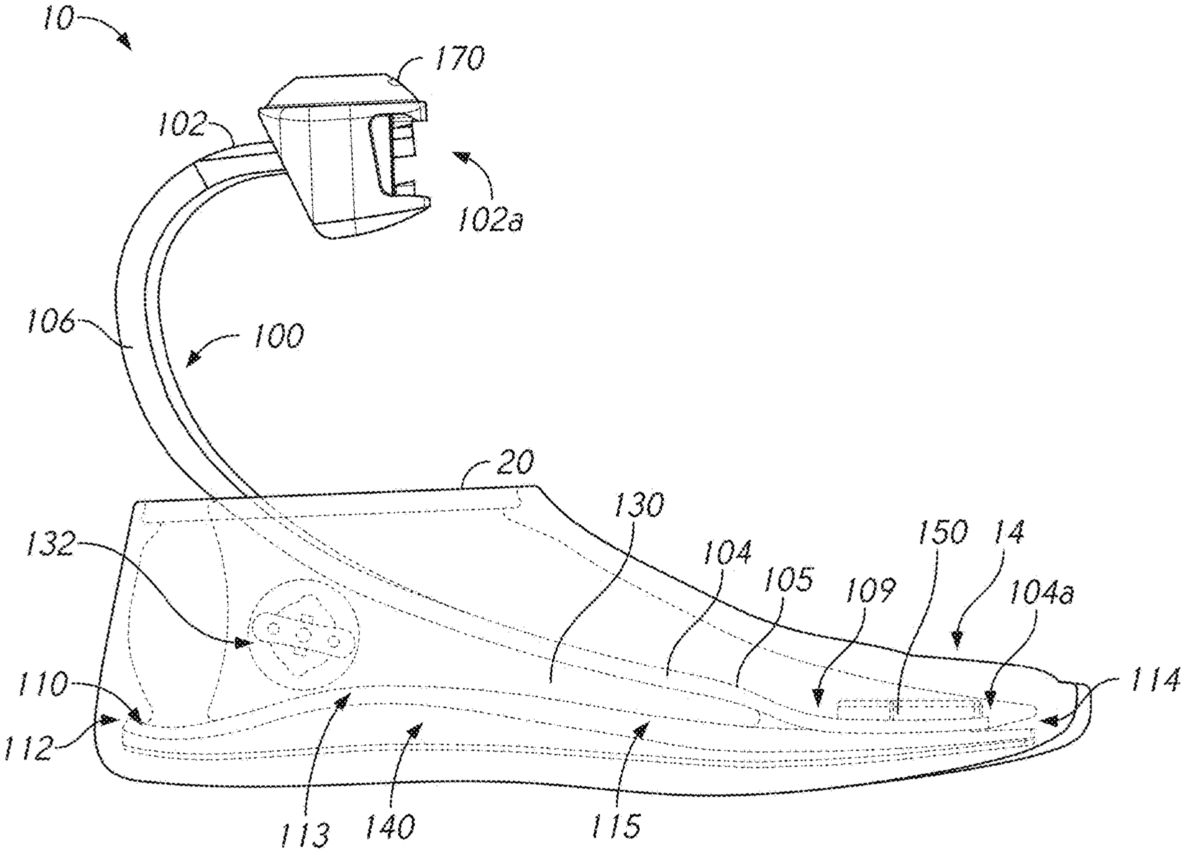
FIG. 1 illustrates an example mechanical prosthetic foot designed for multiple activity levels inside a foot cover.

FIGS. 1-4B and 7A-7C illustrate various aspects of an example prosthetic foot 10. Each of FIGS. 1-4B and 7A-7C does not necessarily show all the features that can be included in the prosthetic foot 10, although the prosthetic foot 10 can include any of the features shown in FIGS. 1-4B and 7A-7C. As shown in FIG. 1, the prosthetic foot 10 can include a first foot member 100 that extends from a proximal section 102 to a distal section 104. The distal section 104 of the first foot member 100 can extend to a distal end 104*a* generally at a location of natural human toes. The proximal section 102 can extend to a proximal end 102*a*. At least a portion of the proximal section 102 closer to the proximal end 102*a* can be coupled to an adapter 170. Having the first foot member 100 extending from the adapter 170 to a toe portion 114 of the prosthetic foot 10 can improve dynamics of the foot by having a long lever through a foot member.

The adapter 170 can include a cavity sized and shaped to receive the at least a portion of the proximal section 102 closer to the proximal end 102*a* of the first foot member 100. The adapter 170 can include a connector, for example a male pyramid connector 172 (see, e.g., FIG. 4), for coupling the prosthetic foot 10 to another prosthetic component, for example, a pylon or socket. The adapter 170 can additionally or alternatively include a different connector than the male pyramid connector 172. In some embodiments, the adapter 170 is monolithic and made of metal. Other materials are also possible.

In the illustrated embodiment, the proximal section 102 can be generally horizontally oriented. The first foot member 100 can have a curved section 106 between the proximal section 102 and distal section 104. The distal section 104 can extend forward and downward from the curved section 106. The distal section 104 can be generally horizontally oriented. The curved section 106 can be generally forwardly-facing concave so that the first foot member 100 in the illustrated embodiment is generally C-shaped. Embodiments of the first foot member can include variations of a generally C shape or forwardly-facing concave shape. In some embodiments, the curved section 106 and/or proximal section 102 can be generally at a location of a natural human ankle. The curved section 106 can have a predetermined length that provides the foot 10 with a desired flexibility. For example, in some embodiments, the curved section 106 can be made more flexible by making it longer while still keeping it within a range of natural human anatomy.

The prosthetic foot 10 can include a second foot member 110. The second foot member 110 can be located below the first foot member 100 when the foot 10 is in a neutral or resting position on a flat surface. The second foot member 110 can extend from a heel end 112 to a toe end 114. The heel end 112 can define a heel end of the prosthetic foot 10. The toe end 114 can define a toe end of the prosthetic foot 10. The second foot member 110 can include an arch region 113 between the heel end 112 and the toe end 114. For example, the arch region 113 can be at approximately the location of an arch of a natural human foot. The second foot member 110 can include a forefoot region 115 distal to the arch region 113 or between the arch region 113 and the toe end 114. The second foot member 110 can be curved upward in the arch region 113 relative to a remainder of the second foot member 110. The upward curve in the arch region 113 can mimic the arch of a natural human foot. A thickness of the second foot member 110 can vary. In the illustrated embodiment, the second foot member 110 can be thicker in the forefoot region 115 and/or at least a portion of the arch region 113. The design of the second foot member 100 can improve the roll-over performance of the prosthetic foot 10.

The first and second members 100, 110 can be plate-like members with generally planar top and bottom surfaces and generally rectangular transverse cross-sections. The first and second members 100, 110 members can be made of lightweight and rigid materials, such as one or more of graphite, fiberglass, carbon fiber, and the like. In some embodiments, the first and second members 100, 110 can each be formed of multiple layers of material that define a monolithic piece.

The first and second members 100, 110 can define a space therebetween in the fore-aft direction. The space can be at a portion of the prosthetic foot 10 that is rear of a toe region of the prosthetic foot 10. In some embodiments, the space can taper toward a toe (or distal) end of the prosthetic foot 10 and have a generally triangular shape. A resilient member 130 can be disposed between the first and second members 100, 110 within the space and occupy at least a portion of the space. The shape of the resilient member 130 can generally follow the shape of the space. The resilient member 130 can generally be a wedge tapering toward the toe end of the prosthetic foot 10. The resilient member 130 can separate a portion of the first and second members 100, 110.

In some embodiments, the resilient member 130 can be removably disposed in the space between the first and second members 100, 110. Optionally, a plurality of resilient members can be disposed in the slot space. In other embodiments, the resilient member 130 can be fixed in the space via, for example, an adhesive. The resilient member 130 can be fixed using an adhesive to the first foot member 100 and/or the second foot member 110. Various other mechanisms can be used to fix the resilient member 130 in the space. For example, the resilient member 130 can be bolted or screwed to the first foot member 100 and/or the second foot member 110. The resilient member 130 can provide additional shock absorption to the prosthetic foot 10. The resilient member 130 can be made, for example, of a hard plastic, such as polyurethane or polypropylene. The resilient member 130 can alternatively be made of a more compressible material than hard plastic, such as foam, natural or synthetic rubbers, elastomer, or the like. The resilient member 130 can be made of any elastic, compressible materials with relatively high amount of rebound, such as carbon blade, high rebound foams, foams with a variable stiffness to change stiffness dependent on impact speed. The resilient member 130 can also be made from a three-dimensional (3D) printed elastic mesh structure that provides an inhomogeneous stiffness transition along the sagittal plane (and also optionally the frontal plane) in order to push the foot 10 during the roll over in a more natural inward outward motion. The resilient member 130 can be made of any other composite, or a spring element (for example, a coil spring, Belleville washers, or the like). The resilient member 130 can be made of any material that provides adequate shock absorption to the prosthetic foot 10.

In some embodiments, a plurality of such resilient members 130 can optionally be provided, with each resilient member having a different stiffness. The resilient member 130 may be split into two sections. The split line may be alongside a frontal plane of the prosthetic foot 10 or in a three-dimensional shape. The two sections can include an upper section and a lower section. The lower section can preferably provide a higher stiffness than the upper section. The stiffness of the lower section can determine whether the proximal section 104 is pushed into a plantarflexion or a vertical deformation.

Examples of a Heel Stiffening Mechanism

In some embodiments, such as shown in FIGS. 1-4B, a heel stiffening mechanism 132 can be embedded within the resilient member 130. The heel stiffening mechanism 132 can be removable and/or replaceable. The heel stiffening mechanism 132 can be located in a more rear portion of the resilient portion. In the illustrated embodiment, the heel stiffening mechanism 132 can be located at least partially above the arch region 113 of the second foot member 110, on a side of the arch region 113 that is closer to the heel end 112 of the second foot member 110.

Figure 2A:
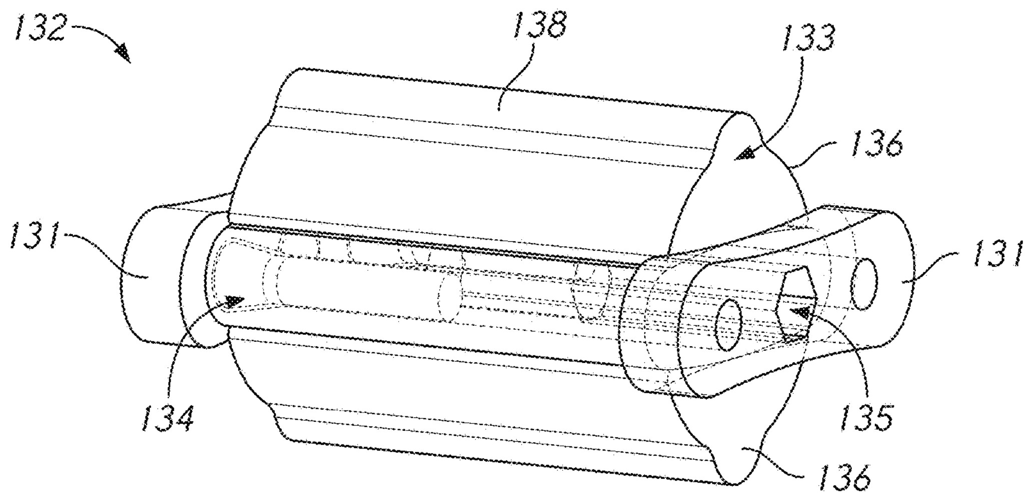
FIG. 2A illustrates an example heel stiffening mechanism of the foot in FIG. 1.

As shown in FIG. 2A, the heel stiffening mechanism 132 can include a rigid inner core 134 sandwiched between two compressible cushions 136. In some embodiments, the compressible cushions 136 can be made of the same material as the resilient member 130. In some embodiments, the compressible cushions 136 can be made of materials that are more compressible or more rigid than the resilient member 130. Non-limiting examples of the materials for the cushions 136 can include polyurethane (PU), thermoplastic polyurethane (TPU) foam, rubber materials, 3D printed elastic grid structures, or any high strength composites, plastics or stiff rubbers (for example, with Shore A Hardness scale greater than 98). The rigid inner core 134 can be made of metal, stiff rubber or plastic, or other suitable materials. The core material can be stiffer than the materials for the cushions and/or the resilient member 130. The core 134 can be generally plate-shaped and can include two generally flat surfaces. Each of the flat surfaces can mate with or abut a flat surface of one of the cushions 136. The cushions 136 can each have a curved surface with a protruding ridge 138 on a side opposite the flat surface.

The heel stiffening mechanism 132 can have a length that is substantially the same as a width of the resilient member 130 measured from a lateral side to a medial side of the resilient member 130. The length of the heel stiffening mechanism 132 allows the heel stiffening mechanism 132 to be accessible from a lateral or medial side of the prosthetic foot 10. The protruding ridges 138 of the cushions 136 can extend along the length of the heel stiffening mechanism. The core 134 can include an elongate tab 131 on each side of the core 134 along the length of the heel stiffening mechanism. The length of the core 134 can be greater than the length of the cushion 136 such that the tabs 131 can extend from each side of the cushion 136 along the length of the heel stiffening mechanism 132. Each of the elongate tab 131 can protrude at least partially from an end surface 133 of the cushion 136. A length of the elongate tab 131 can be greater than a width of the cushion 136 such that the tab 131 protrudes from one or both ends of the cushions 136 along the width of the cushion 136. When embedded in the resilient member 130, the elongate tabs 131 of the inner core 134 can be generally parallel to a sagittal plane of the prosthetic foot 10. When viewed from the lateral or medial side of the prosthetic foot 10, the ridges 138 of the cushion 136 can be symmetrically positioned about a longitudinal axis of the elongate tab 131 of the core 134.

Figure 2B:
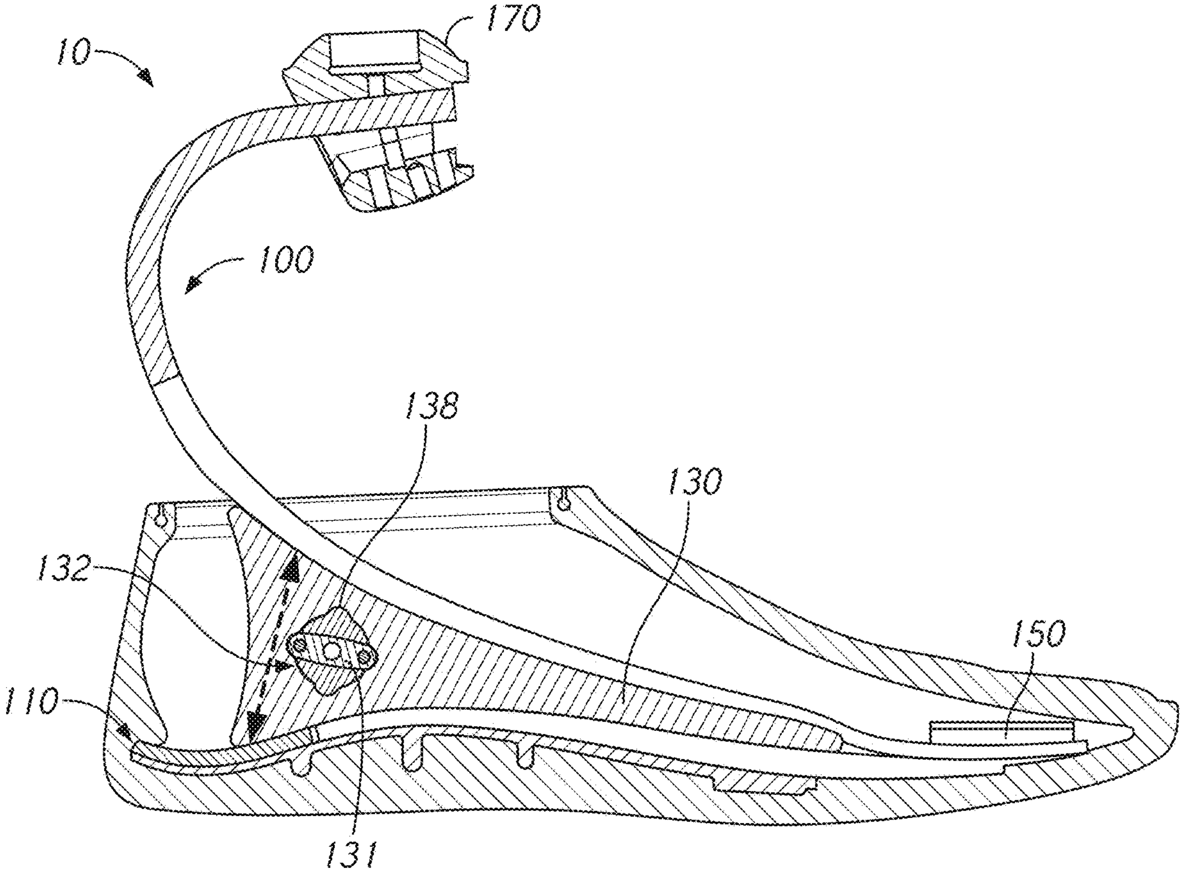
FIGS. 2B and 2C illustrate two different example configurations of the heel stiffening mechanism.
Figure 2C:
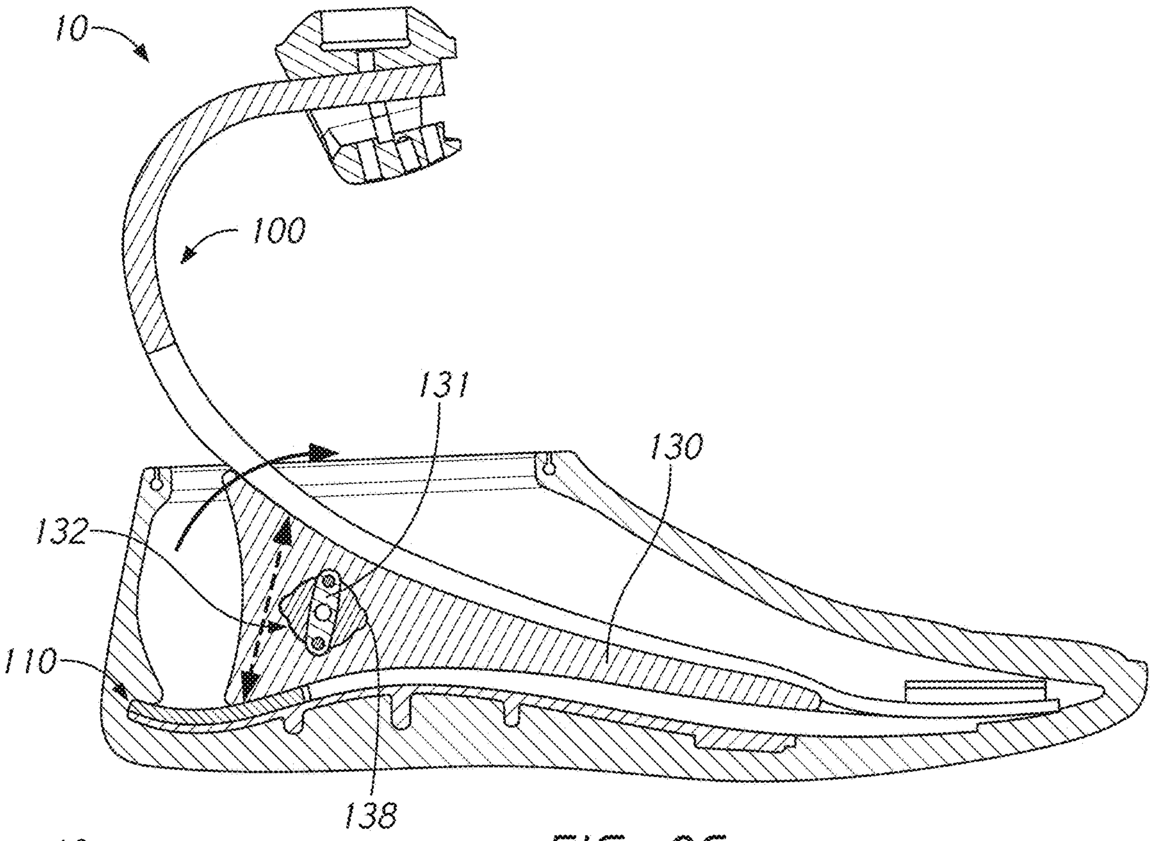

As shown in FIGS. 2B and 2C, when viewed from the lateral or medial side of the prosthetic foot 10, the heel stiffening mechanism 132 can have at least two configurations, each configuration having a different defined or locked position of the elongate tab 131 (and of the ridges 138) relative to the prosthetic foot 10. As shown in FIG. 2B, in a first defined position, the elongate tab 131 can be generally perpendicular to the double arrow. The elongate tab 131 can be generally horizontal in the first defined position. An imaginary line connecting the ridges 138 can be generally parallel to the double arrow. The double arrow can indicate a direction of a reaction force when the foot 10 is resting on a flat surface. The double arrow is slanted slightly forward relative to a vertical line when the foot 100 is resting on a flat surface. In the first defined position, the heel stiffening mechanism 132 contributes to a first stiffness of a heel portion of the prosthetic foot 10. As shown in FIG. 2C, in a second defined position, the elongate tab 131 can be generally parallel to the double arrow. The elongate tab 131 can be more vertically slanted in the second position than in the first position. An imaginary line connecting the ridges 138 can be generally perpendicular to the double arrow. In some embodiments, the elongate tab 131, also referred to as a rotary switch, can have at least two defined positions, the first position and the second position as disclosed herein, depending on whether the tab 131 rests in a square hole or a round hole with slots. When the elongate tab 131 is in the first position, the resilient member 130 can have relatively low resistance to vertical deflection. In the second defined position, the heel stiffening mechanism 132 contributes to a second stiffness of the heel portion of the prosthetic foot 10. The second stiffness is higher than the first stiffness. Rotating the elongate tab 131 from the first position to the second position reduces the vertical deflection of the resilient member 130, which leads to a higher stiffness of the heel portion of the prosthetic foot 10. The foot can bear a greater weight when the heel stiffening mechanism 132 is in the second position. In the second position, the elongate tab is generally parallel to the double arrow, rather than being perpendicular to a flat surface on which the foot 10 is resting so as to avoid a resultant bending moment in the foot 10. Such a bending moment can cause a toe portion of the prosthetic foot 10 to have a tendency to tilt upward from the flat surface.

The prosthetic foot 10 can have a softer heel in the first configuration and a stiffer heel in the second configuration. In some embodiments, the prosthetic foot 10 can be more suitable for walking when the heel stiffening mechanism is in the first configuration, with the elongate tab 131 in the first defined position. In some embodiments, the prosthetic foot 10 can be more suitable for lifting heavy objects when the heel stiffening mechanism is in the second configuration, with the elongate tab 131 in the second defined position. The higher stiffness in the heel can prevent the first foot member from sinking into or toward the second foot member.

The heel stiffening mechanism 132 can be rotated about 90 degree in the clockwise direction about its central longitudinal axis, as shown in FIG. 2C, to transform from the first configuration to the second configuration. Alternatively, the heel stiffening mechanism 132 can be rotated by about 90 degree in the counterclockwise direction about its central longitudinal axis to transform from the first configuration to the second configuration. Optionally, the heel stiffening mechanism 132 can be rotated in either or both the clockwise or the counterclockwise direction by a different amount than 90 degree, for example, about 30 degree, about 45 degree, about 60 degree. In another embodiment, the heel stiffening mechanism can be rotated in either or both the clockwise or the counterclockwise direction by any amount between 0 and 90 degree. The heel stiffening mechanism 132 contributes to a stiffness that is between the first and second stiffness to the heel portion of the prosthetic foot 10 when the heel stiffening mechanism 132 is rotated to any position between the first and second defined positions. Transitions between the different positions between the first and second defined positioned can be stepwise or gradual (or smooth). The heel stiffening mechanism 132 can contribute to a different stiffness to the heel portion of the prosthetic foot 10 at each different position relative to the prosthetic foot 10.

The heel stiffening mechanism 132 can be rotated manually using a lever, a hex key, or any other suitable tool, or by hand without any tools. In one embodiment such as shown in FIG. 2A, the tab 131 may include a corresponding hex key interface 135 that can receive the hex key to rotate the heel stiffening mechanism 132 about its central longitudinal axis. By rotating the elongate tab 131, the entire heel stiffening mechanism 132 can be rotated as a single unit. As described above, the heel stiffening mechanism 132 can be embedded in a cavity of the resilient member 130. In some embodiment, no bushings or other lining is required for embedding the heel stiffening mechanism 132 in the resilient member 130. The cavity can include indentations sized to accommodate the ridges 138 and/or the ends of tabs 131 extending outward from ends of the cushions 136 along the width of the cushion 136. The indentations can be located along a circumference of the cavity. In some embodiments, the indentations can be uniformly spaced out along the circumference of the cavity. In the illustrated examples such as shown in FIGS. 2B and 2C, the cavity can include four indentations uniformly spaced out along the circumference of the cavity to lock the heel-stiffening mechanism 132 in the first or second configuration. The ridges 138 and/or the wall of the cavity can be compressed when the heel stiffening mechanism 132 is being rotated between the first and second configurations. In other embodiments, the cavity can include more than four indentations along the circumference of the cavity so as to allow for more defined or locked positions than the first and second defined or locked positions as shown in FIGS. 2B and 2C.

Various Examples of the Resilient Member

Figure 5A:
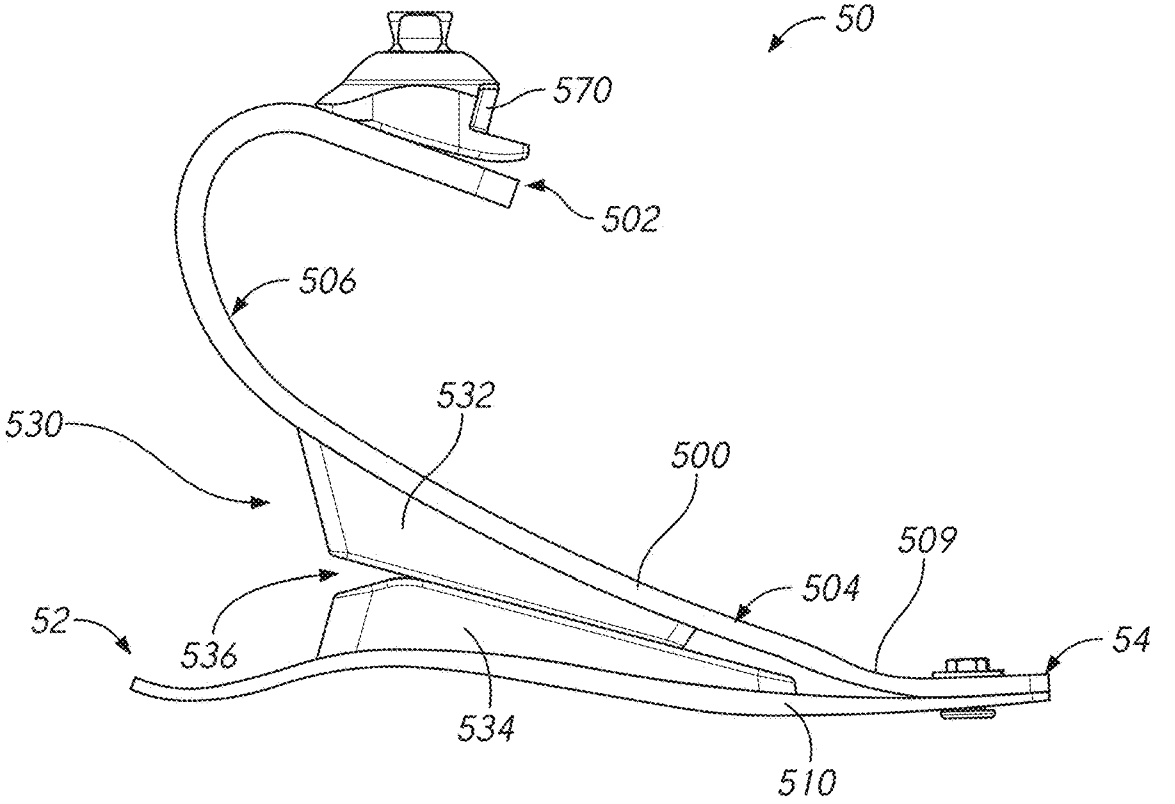
FIG. 5A illustrates another example mechanical prosthetic foot designed for multiple activity levels including a different resilient member than the foot of FIG. 1.
Figure 5B:
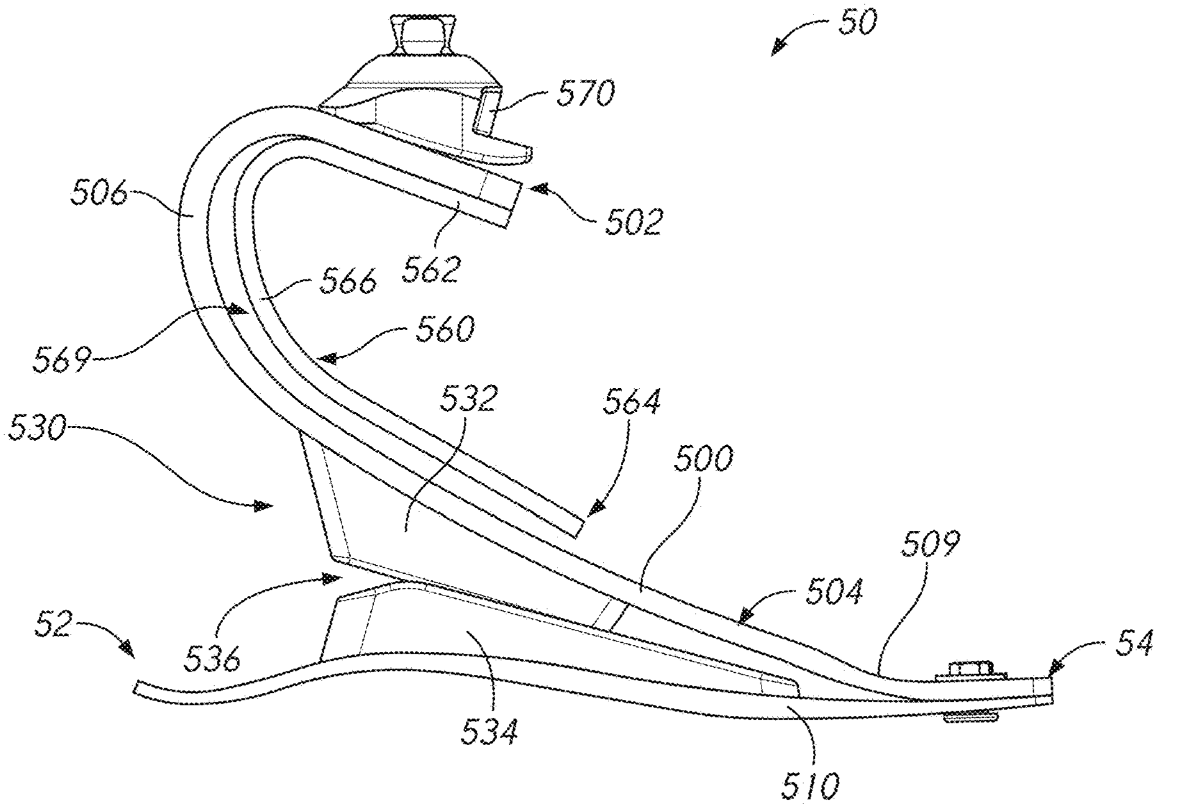
FIG. 5B illustrates a variation of the mechanical prosthetic foot of FIG. 5A.
Figure 5C:
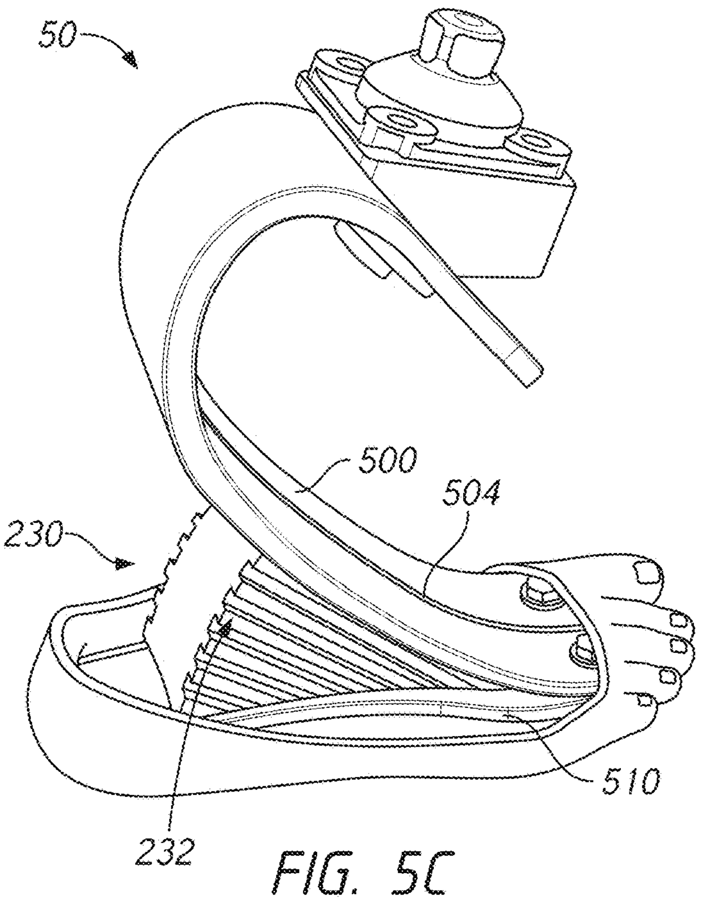
FIG. 5C illustrates another example mechanical prosthetic foot designed for multiple activity levels including a different resilient member than the foot of FIG. 1.

FIGS. 5A-5C illustrate a prosthetic foot 50 that can include any of the features of the prosthetic foot 10, with the differences noted in the description of FIGS. 5A-5C. Any of the features of the prosthetic foot 50 can also be incorporated into the prosthetic foot 10. As shown in FIGS. 5A, 5B, and 5C, the prosthetic foot 50 can include a first foot member 500 that extends from a proximal section 502 to a distal section 504. The first foot member 500 can have a curved section 506 between the proximal section 502 and distal section 504. The distal section 504 can extend forward and downward from the curved section 506. The distal section 504 can be generally horizontally oriented. The curved section 506 can be generally forwardly-facing concave so that the first foot member 500 in the illustrated embodiment is generally C-shaped or any other suitable shapes. The distal section 504 of the first foot member 500 can extend to a distal end generally at a location of natural human toes. The proximal section 502 can extend to a proximal end. At least a portion of the proximal section 502 closer to the proximal end can be coupled to an adapter 570. Rather than being generally horizontal, the proximal section 502 of the first foot member 500 can angle downward toward the distal section 504. The downward angling of the proximal section 502 can increase a length of the first foot member 500, allowing the first foot member 500 to contain more material, for example, the carbon fibers or other suitable materials disclosed herein. The downward angling of the proximal section 502 can additionally allow the foot 50 to be oriented better for running motion. The effective lever arm of the foot 50 extends from the toe portion 54 of the foot 50 to a point furthest away, and is therefore longer, than if the proximal section 502 is generally horizontal. The downward angle of the proximal section 502 can also reduce a build height of the prosthetic foot 50 than if the proximal section 502 is generally horizontal. In some embodiments, the angling downward design of the proximal section 502 is preferred. Additionally or alternatively, as shown in FIG. 5B, the lever arm can be increased by moving the curved section 506 of the first foot member 500 more towards the heel portion 52 than the curved section 506 as shown in FIG. 5A. The curved section 506 in FIG. 5B starts on the first foot member 500 at a more proximal location than the curved section 506 in FIG. 5A. For example, the distal section 504 of the first foot member can be longer to move the curved section 506 more proximally.

In some embodiments, such as shown in FIGS. 5A and 5B, the resilient member 530 between the first foot member 500 and the second foot member 510 can include a first resilient component 532 and a second resilient component 534. The first and second resilient components 532, 534 can each be attached to one of a surface of the second foot member 510 or the first foot member 500. In some embodiments, the first and/or second resilient components 532, 534 can be wedge-shaped (e.g., tapering toward a distal end of the first and/or second resilient members 532, 534). In some embodiments, the first resilient member 532 can extend distally of the second resilient member 534. In some embodiments, the second resilient member 534 can extend distally of the first resilient member 532. The first resilient component 532 can be located closer to the first foot member 500. The second resilient component 534 can be located closer to the second foot member 510. When the prosthetic foot 500 is resting on a flat surface, the first resilient component 532 can be located generally above the second component member 534. In some embodiments, the first and second resilient components 532, 534 can have different stiffness values. The first resilient component 532 can be stiffer than the second resilient member 534, or the second resilient component 534 can be stiffer than the first resilient member 532. In some embodiments, the first and second resilient components 532, 534 can have the same stiffness. The prosthetic foot 50 can experience different stiffness values at different stages of the gait cycle due to the different stiffness values of the first and second resilient components 532, 534. Splitting the resilient member 530 into the first and second resilient components 532, 534 can also reduce noise due to movement of the prosthetic foot 50 if debris (for example, dust or stones) is stuck between the first and second resilient components 532, 534. For example, after toe-off during walking, the first and second resilient components 532, 534 can contact each other as the distance between the first and second foot members 500, 510 decreases. If debris is collected between the first and second foot members 500, 510, movement of the foot 50 after toe-off can be noisy. With the resilient member 530 formed by upper and lower components 532, 524, noise due to the debris collected between the first and second foot members 500, 510 can be reduced. The debris can be removed by the user or fall out on its own.

Figure 6:
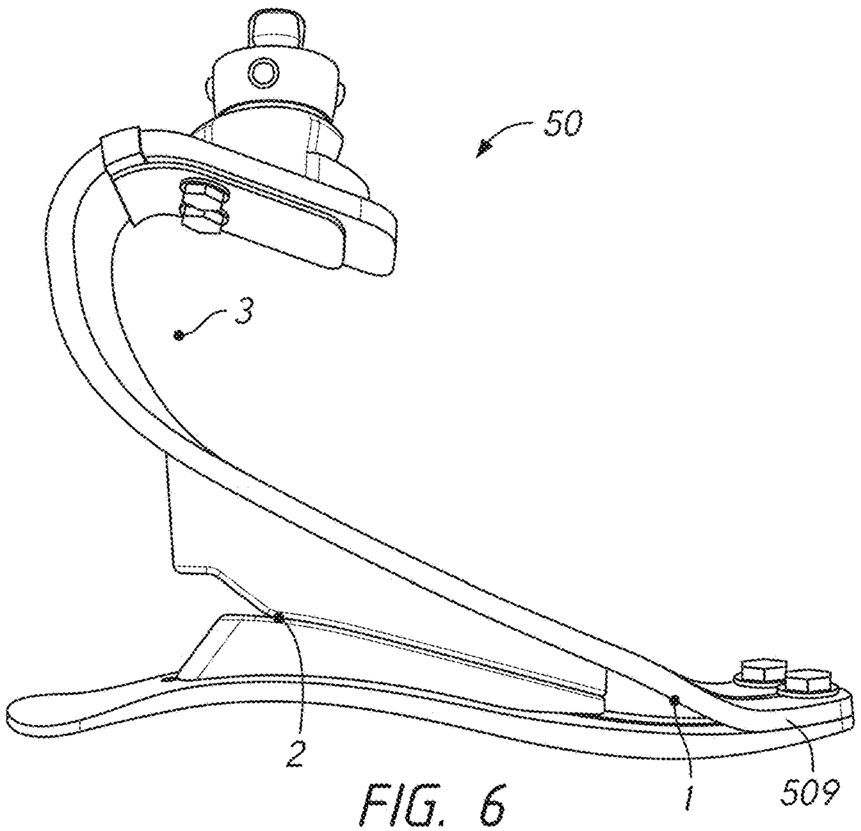
FIG. 6 illustrates various pivot points of the mechanical prosthetic foot of FIG. 5A.

The thicknesses of the first and second resilient components 532, 534 may vary and may differ from the first and second resilient components 532, 534 as depicted in FIGS. 5A, 5B, and 6. In some embodiments, one of the first and second resilient components 532, 534 can be thicker than the other component. In other embodiments, the resilient member can include three or more components. In some embodiment, the resilient member can be made of a single component. All these variations of the resilient member can achieve the functionality and interaction between the resilient member and the foot members described below.

The shape of the first and second resilient components 532, 534 can be designed so that the prosthetic foot can both be pushed in a plantarflexion and also in a vertical displacement to stiffen up and provide some shock absorption during heel strike. Bending of the prosthetic foot to push the foot into plantarflexion may be limited to a predetermined range, for example, not greater than 5°, or 8°, or 10°. The shape of the first and second resilient components 532, 534 can be designed to provide a high surface area so as to reduce the surface stress, which can increase the endurance of the different parts of the prosthetic foot. The first and second resilient components 532, 534 can engage each other after midstance, which can influence the heel and toe stiffness of the prosthetic and thus the bending of the first foot member. The relative positions of the first and second resilient components 532, 534 can influence the performance of the foot. The relative positions of the first and second resilient components 532, 534 can be adjusted by the user. Depending on which resilient component has its distal end closer to the toe region of the foot, the distal portion of that resilient component can function as a vertical end stop during either vertical impact, or any higher impact activity (for example, running, jumping, or otherwise) and landing around a mid-foot region or a toe region.

The first resilient component 532 can move around two pivot points of the second resilient component 534, which can determine the foot motion during heel strike. The second resilient component 534 can be shaped so that vertical compression of the second resilient component 534 can lead to a shear in the second resilient component 534. The shear can allow for a forwardly pointing expansion of the second resilient component 534, thereby leading to a more aggressive transition of the center of pressure of the prosthetic foot from the heel end toward the toe end and avoiding an upwards motion of the prosthetic foot during midstance. When transitioning from fast walking (or any other lower impact activity) to running (or any other higher impact activity), any two-component resilient member disclosed herein can provide impact cushioning and still being capable of moving forward the center of pressure of the prosthetic foot during the compression. The force returning the second resilient member 534 to its uncompressed shaped can push the prosthetic foot 50 up and forward.

Figure 5D:
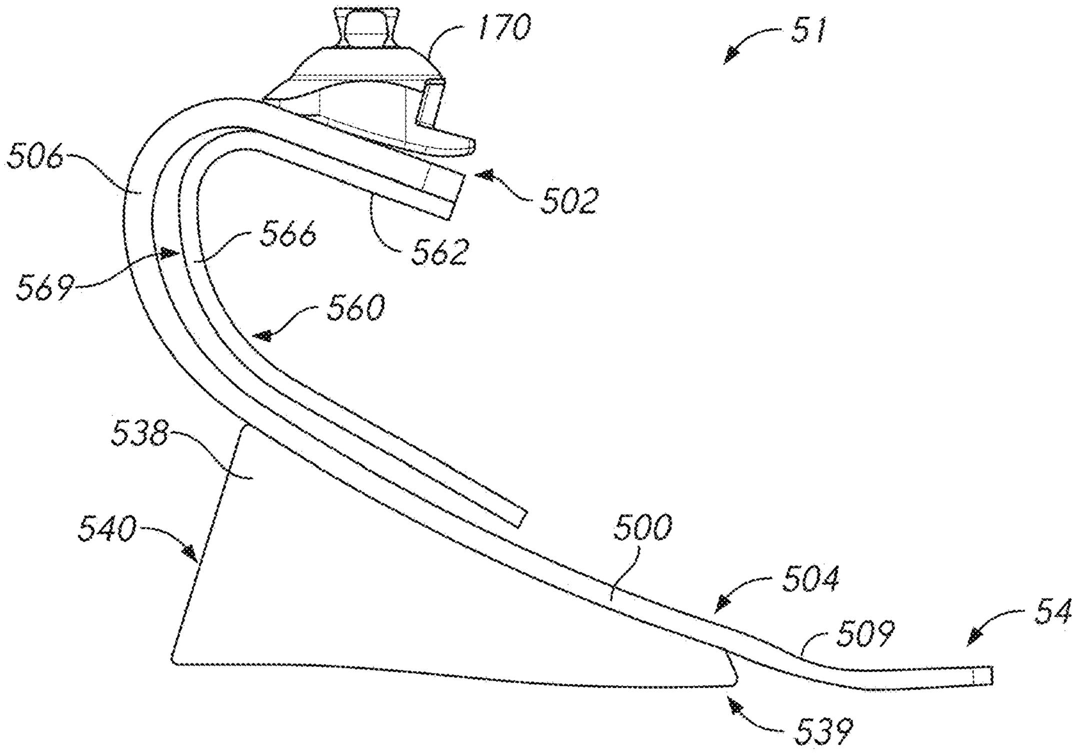
FIG. 5D illustrates a variation the mechanical prosthetic foot of FIG. 5B with a heel bumper.
Figure 5E:
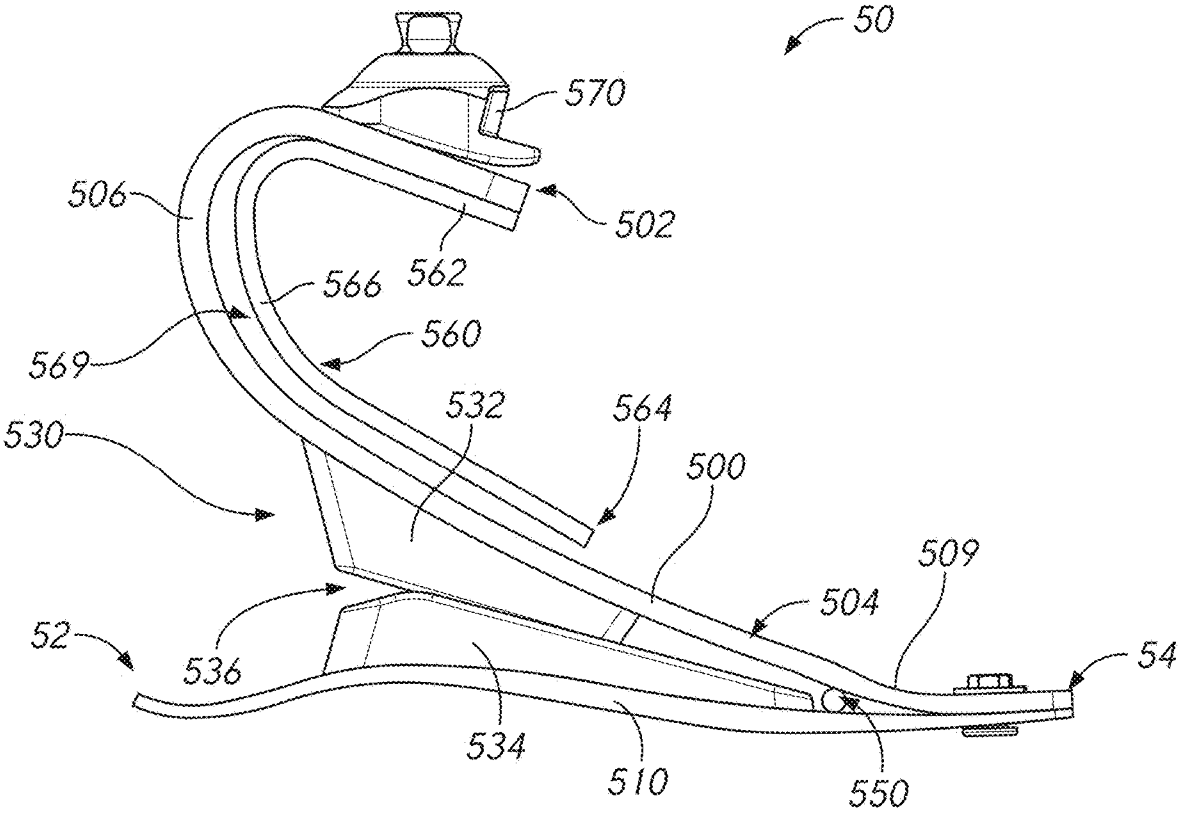
FIG. 5E illustrates a variation of the mechanical prosthetic foot of FIG. 5B with a stiffening rod.

In some embodiments, the prosthetic foot examples disclosed herein can include a stiffening member (for example, a stiff PU rod or any other material with a stiffness higher than the resilient components 532, 534) between the first and second foot members. The location of the stiffening member can vary. FIG. 5E illustrates an example location of the stiffening member 540. As shown in FIG. 5E, the stiffening member 540 can be located closer to the toe portion 54 than the resilient members 532, 534. The stiffening member 540 is illustrated to have a generally circular cross-section, but can be of any other suitable shape cross-sectionally, for example, elliptical, tear-drop, or otherwise. In some embodiments, the stiffening member can include a polyurethane rod. The stiffening member can provide a pivot point about which the first foot member can bend. The stiffening member can create a defined bending of the first foot member around a specific pivot point, in addition to the resilient member, which can provide a vertical cushioning effect while also contributing to the plantarflexion of the foot. The stiffening member can provide better control to define the bending of the first foot member, while the resilient member can play a more supportive role.

As shown in FIGS. 5A and 5B, one of the first or second resilient components 532, 534 can include a cutout portion 536. In the illustrated embodiment, the cutout portion 536 is located on the first resilient component 532 at or near the interface between the first and second resilient components 532, 534. The cutout portion 536 can be located closer to the heel portion 52 of the prosthetic foot 50 than to the toe portion 54 of the prosthetic foot 50. In the illustrated embodiment, the cutout portion 536 can extend from a proximal end of the resilient member 530, such as a proximal end of the first resilient component 532. The placement of the cutout portion 536 can vary and can determine the stiffness of the heel portion 52 of the prosthetic foot 50, and/or the amount of travel that either plantarflexes the foot 50 or displaces the foot 50 vertically. The cutout portion 536 can function as a pivot point for the first and/or second foot members 500, 510, pushing the foot 50 into an active plantarflexion. The cutout portion 536 can be triangular or wedge-shaped, or any other shape. The cutout portion 536 can be oriented so that a height of the cutout portion 536 decreases toward the toe portion 54 of the prosthetic foot 50.

The shape of the first or upper resilient component 532 can allow for adjustment to tolerance changes in production. For example, to accommodate tolerance in the thickness of the first and/or second foot members 500, 510, the first resilient component can be attached (for example, glued) closer or further away from the toe portion 54 of the foot 50.

Figure 4A:
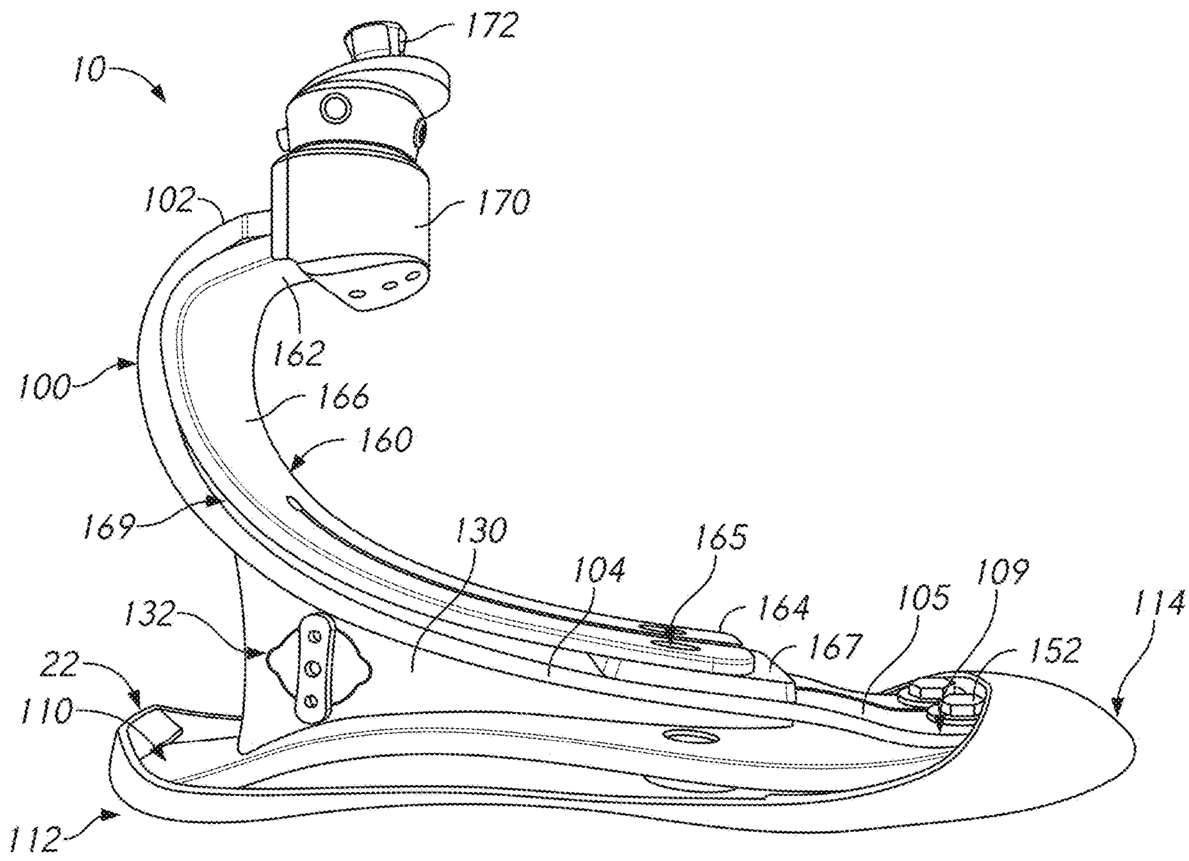
FIG. 4A illustrates an example mechanical prosthetic foot designed for multiple activity levels inside a different foot cover than the foot cover in FIG. 1.
Figure 4B:
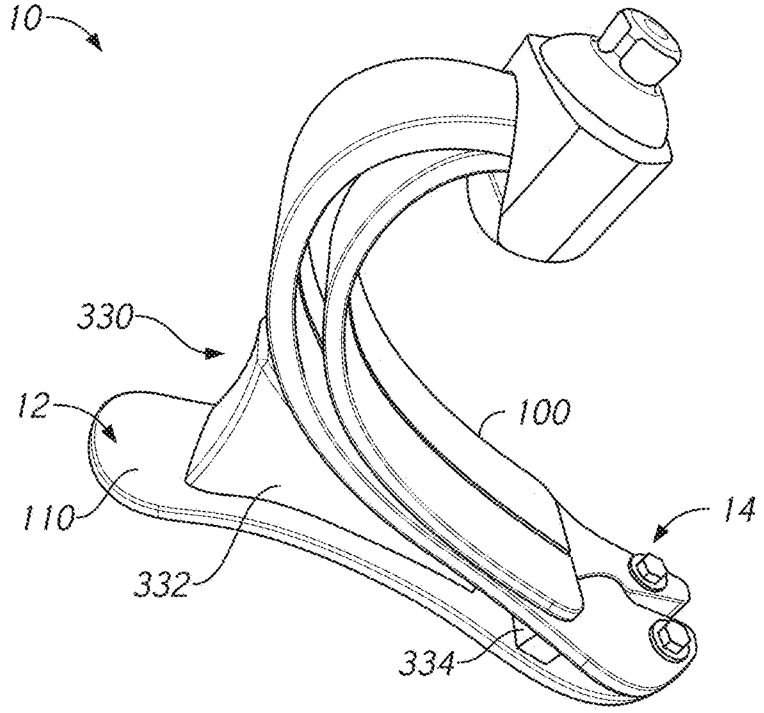
FIG. 4B illustrates another example mechanical prosthetic foot designed for multiple activity levels including a different resilient member than the foot of FIG. 1.

The shape of the second or lower resilient component 534 can be designed to extend further to the toe portion 54 (with one example shown in FIG. 4B). The second resilient component 534 being closer to the toe portion 54 can provide an end stop, for example, during high vertical impact loading, and/or to help the first and/or second foot members 500, 510 to stiffen up near a portion of the foot 50 that corresponds to a metatarsal region of a human foot. The end stop can reduce the range of bending of the first foot member 500, causing the bending to move forward (or more distally). In some embodiments, the resilient member can occupy an entirety of the space between the first and second foot members rearward of a coupling location of the first and second foot members.

The resilient member 530 can be shaped three-dimensionally in order to achieve a more biomechanically appropriate progression of the center of pressure of foot 50 from an outer contour of the heel portion 52 of the foot 50 over to the toe portion 54 of the prosthetic foot 50. The mating surfaces of the resilient member 530 with the first and/or second foot members 500, 510 can be shaped three-dimensionally to push the foot 50, for example, inwardly to a location of the prosthetic foot 50 that corresponds to the human big toe during roll-over. The mating surfaces of the resilient member 530 can be shaped in order to allow for more progressive dampening characteristics and/or to result in different deformation behaviors pushing the foot 50 more forward than upward.

In some embodiment, such as shown in FIG. 5C, a resilient member 230 can be located between the first foot member 500 and the second foot member 510. The resilient member 230 can include multiple grooves 232 on one or both lateral sides of the resilient member 230. The grooves 232 can run along a length of the resilient member 230. In some embodiments, the grooves 232 can run generally parallel to the distal section 504 of the first foot member 500. In some embodiments, the grooves 232 can have a depth of about 1 mm to about 2 mm, or more. In some embodiments, the grooves can extend substantially through an entirety of the length of the resilient member 230. The grooves 232 can reduce the stiffness of the resilient member 230, accommodating a softer impact on the prosthetic foot 50 and/or a more progressive loading on the prosthetic foot 50. The grooves 232 can additionally allow different deformation and unloading characteristics of the resilient member 230, pushing the foot 50 more forward. The resilient member 230 can include any of the feature of the resilient member 130, 530 described above. The resilient member 130, 530 can include the grooves as shown in the resilient member 230.

In some embodiments, such as shown in FIG. 4B, a resilient member 330 can be between the first foot member 100 and the second foot member 110 of the prosthetic foot 10. The resilient member 330 can include a first resilient component 332 and a second resilient component 334. The first resilient component 332 can have any of the features of the resilient member 130, 230 described above. The first resilient component 332 can be located more rearward than the second resilient component 334. The second resilient component 334 can be made of or include a stiffer material than the first resilient component 332. The second resilient component 334 can be located behind a toe portion 14 of the prosthetic foot 10. The second resilient component 334 can act as a rotation or pivot point, similar to the pivot point created by the cutout portion in the first or second resilient component 532, 534 described above with reference to FIGS. 5A and 5B. For the second resilient component 334, a distal edge and/or the proximal edge of the member 334 defines the pivot point of the first and/or second foot members 100, 110. The second resilient component 334 can additionally provide greater contact between the first and/or second foot members 100, 110 and a higher stiffness of the prosthetic foot 10 closer to the toe portion 14 of the prosthetic foot 10, similar to the function of a more forward second resilient component 534 as described above with reference to FIGS. 5A and 5B.

Examples of Prosthetic Feet with a Sole Portion

Figure 3:
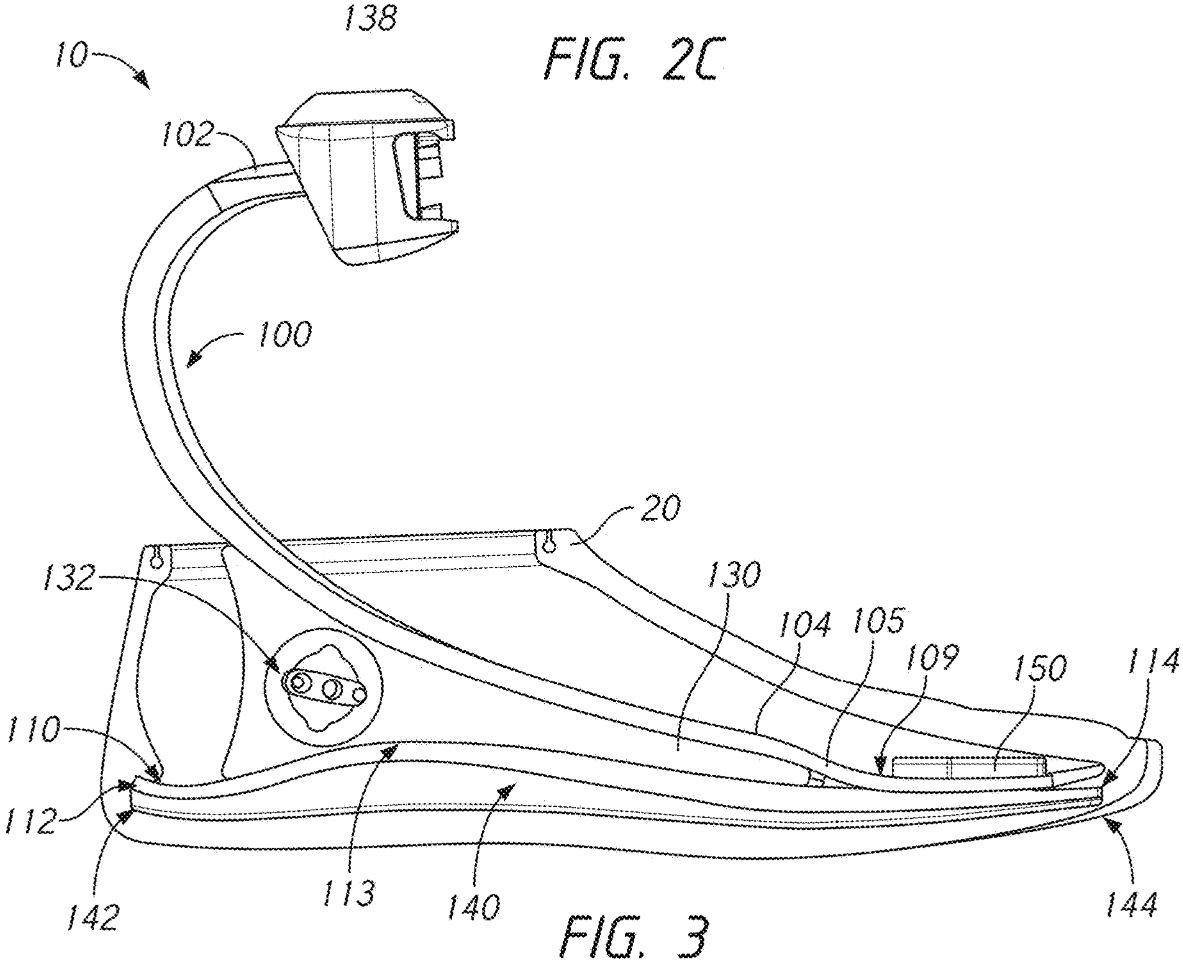
FIG. 3 illustrates a cross-sectional view of the prosthetic foot and foot cover in FIG. 1.

In some configurations, the prosthetic foot 10 can be used without the foot cover 20. For example, a prosthetic foot designed for running typically does not require a foot cover and/or a shoe. Alternatively, the prosthetic foot disclosed herein can be removed from the foot cover easily to be rinsed or cleaned. However, the first and second foot members 100, 110, which are typically made of carbon fiber, may slip when using the foot 10 without the foot cover 20. Additionally, the lack of the foot cover 20 can result in the prosthetic foot not providing adequate three-dimensional roll-over. In some embodiments such as shown in FIGS. 1 and 3, a sole portion 140 can be attached to a bottom or lower surface of the second foot member 110. The sole portion 140 can include a toe end 144 and a heel end 142. The sole portion 140 can be aligned to the second foot member 110. The toe end 144 of the sole portion 140 can align with the toe end 114 of the second foot member 110. The heel end 142 of the sole portion 140 can align with the heel end 112 of the second foot member 110. In some embodiments, the sole portion 140 does not extend past the heel end 112 and/or the toe end 114 of the second foot member 110. In other embodiments, the sole portion 140 can extend slightly forwardly of the toe end 114 and/or slightly rearwardly of the heel end 112 of the second foot member 110. The sole portion 140 can have an outer shape corresponding to the outer shape of the second foot member 110. For example, the sole portion 140 can have a rounded edge corresponding to a rounded edge of the toe end 114 of the second foot member 110 (see, e.g., FIG. 7C).

In the illustrated embodiment, the sole portion 140 can have a varying thickness. As shown in FIG. 3, the sole portion 140 can have a decreasing thickness toward the toe end 114 and the heel end 112 of the second foot member 110. The sole portion 140 can be the thickest at or near the arch region 113 of the second foot member 11. The thickness of the sole portion 140 can generally follow a curvature of the bottom or lower surface of the second foot member 110. The bottom or lower surface of the sole portion 140 can be generally flat or complementary to an inner sole surface of the foot cover 20. The varying thickness of the sole portion 140 can facilitate a smooth three-dimensional roll-over of the prosthetic foot 10. In other embodiments, the sole portion 140 can have a uniform thickness.

The sole portion 140 can have anti-slip property. For example, the sole portion 140 can be a pad or cushion made of a compressible or resilient material, such as rubber, plastic, or elastomer. In some embodiments, a bottom or lower surface of the sole portion 140 can be patterned to further improve the anti-slip property of the sole portion 140. With the sole portion 140, the prosthetic foot 10 can be worn without the foot cover 20, which can make it easier to clean the foot 10 and/or allow easier access to the heel stiffening mechanism 132 to adjust the heel stiffness of the prosthetic foot 10. In some embodiments, the sole portion 140 can be attached to the second foot member 110 with an adhesive. However, other attachment mechanisms can be used, such as bolts, screws, clamps, and/or bands wrapped around the sole portion 140 and the second foot member 110.

In some embodiments, such as shown in FIG. 4, the prosthetic foot 10 can be inserted into a foot cover 22 with a lower profile than the foot cover 20 shown in FIGS. 1-3. The lower profile foot cover 22 can wrap around the heel end 112 of the second foot member 110 and the toe end 114 of the second foot member 110 as well as the distal end 104 of the first foot member 100. A sole portion such as described above can be integrated into the lower profile foot cover 22. The foot cover 22 can leave a remainder of the prosthetic foot 10 uncovered.

Examples Toe and/or Forefoot Features of a Prosthetic Foot

In some embodiments such as shown in FIGS. 1, 2B, 2C, 3, and 4A, the distal section 104 of the first foot member 100 can include a change in curvature so that the distal section 104 has a segment 105 of downward curvature and a toe section 109 that is downwardly vertically offset from the remainder of the first foot member 100 proximal to the toe section 109.

In some embodiments, a distance of the vertical offset is in the range of about 0 mm to about 15 mm, or about 0 mm to about 10 mm. In some embodiments, the segment 105 of downward curvature can be short so that the change in curvature is a step-like change. In other embodiments, the segment 105 can be slightly longer so that the change in curvature is a more gradual change. In some embodiments, the segment 105 of downward curvature is in a location corresponding to the metatarsal joint in a natural human foot.

The distal section 104 of the first foot member 100 can be generally concave on both the proximal and distal sides of the segment 105 of downward curvature. In some embodiments, a radius of curvature of the distal section 104 of the first foot member 100 is the same on the proximal and distal sides of the segment 105 of downward curvature so that the only change in the distal section 104 of the first foot member 100 is the vertical offset. In other embodiments, the radius of curvature of the distal section 104 is different on the proximal and distal sides of the segment 105 of downward curvature. The radius of curvature on the distal side of the segment 15 of downward curvature can be chosen to promote a smooth roll-over of the first foot member 100 during ambulation.

In some embodiments, the prosthetic foot can further include a toe piece under a toe region of the second foot member. The toe piece can help to increase the loading of the first foot member as the toe piece can initiate loading of the first foot member earlier. The toe piece can be attached to a bottom surface of the toe region of the second foot member using adhesives. Alternatively, the toe piece can be integrated as part of the second foot member. The toe piece can have an outer shape that follow an outer shape of the toe region of the second foot member.

As shown in FIGS. 1, 3, and 4A-B, in some embodiments, the first foot member 100 is coupled to the second foot member 110 in the vertically offset toe section 109 of the first foot member 100. The coupling can allow for motion and bending of the coupled first and second foot members 100, 110 in a location corresponding to a toe region of a natural human foot, which is generally in the area of the vertically offset (also referred to as drop-down) toe section 109. The motion and bending of the coupled portion of the first and second foot members 100, 110 can facilitate dorsiflexion of the foot 10 while keeping the heel portion of the foot 10 on the flat surface. The coupled portion of the first and second foot members 100, 110 can also function like a metatarsal joint of a natural human foot.

Additionally, in some embodiments, the second foot member of the prosthetic foot disclosed herein can include a vertical offset in the toe region (also referred to as a "drop toe section"). The vertical offset in the toe region of the second foot member can increase the loading on the first foot member.

In some embodiments, the prosthetic foot may not include a separate second foot member because a heel portion of the prosthetic foot is permanently connected to an upper foot portion at a toe end or toe region of the prosthetic foot. The heel portion and the generally C-shaped portion can be continuous at the toe end to form a single foot member. For example, the prosthetic foot can include a foot member that can include a generally C-shaped portion that turns rearward at a toe end of the generally C-shaped portion to form a heel portion. In some other embodiments, the heel portion of the foot member can be laid up onto the generally C-shaped portion so that a toe section of the heel portion and a toe section of the generally C-shaped portion are molded together. Such embodiments of the prosthetic foot can have any of the features of the prosthetic foot examples disclosed herein (for example, in FIGS. 1, 4A, 4B, 5A, 5B, 7A), except that a fastener at the toe end would not be necessary.

In some embodiments, the prosthetic foot can include a heel bumper placed under a generally C-shaped foot member. FIG. 5D illustrates an example prosthetic foot 51 that includes a heel bumper 538. The prosthetic foot 51 can include any of the features of the prosthetic foot 50 as shown in FIGS. 5A and 5B. For example, the prosthetic foot 51 can include an adapter 570 and a generally C-shaped first foot member 500 that are substantially the same as the adapter 570 and the first foot member 500, respectively, of the prosthetic foot 50 as shown in FIGS. 5A and 5B. The prosthetic foot 51 can optionally include a second foot member 560 that is substantially the same as the third foot member 560 as shown in FIG. 5B (which are described in greater detail below). The heel bumper 538 can be placed on a bottom surface of the first foot member 500. The heel bumper 538 can have generally a wedge shape. A top surface of the heel bumper 538, which is the surface that contacts the first foot member 500, can be generally forwardly-facing concave to match a shape of the curved section 506 of the first member 500. A bottom surface of the heel bumper 538 can be generally level with a bottom surface of the toe section of the first foot member 500 when the prosthetic foot 51 is at rest. The prosthetic foot 51 may not include a foot member below the first foot member 500. Therefore, the bottom surface of the heel bumper 538 and the bottom surface of the toe section of the first foot member 500 can contact a ground surface when the prosthetic foot 51 is in use. The length of the heel bumper 538 can vary. In the illustrated embodiment, the heel bumper 538 can have a distal end 539 at or near the distal section 504 of the first foot member 500. The heel bumper 538 can have a heel end 540 that can be more posterior than the adapter 570 or approximately aligned with a posterior end of the adapter 570 when the prosthetic foot 51 is at rest. In some embodiments, the heel bumper 538 can have a stiffness or be made of the same material as the resilience member 530 of the prosthetic foot 50 as shown in FIGS. 5A and 5B.

In some embodiments, the prosthetic foot may include a generally C-shaped first foot member and a loose second foot member placed under the first foot member. The loose second foot member may be held together with the first foot member by a foot cover and may not be otherwise connected to the first foot cover. In some embodiments, the prosthetic foot may include first and second foot members, but the first and second foot members may be connected at a location more proximal than the toe section. For example, the second foot member may have a distal end that terminates proximal to the toe end of the prosthetic foot. The distal end of the second foot member may be connected to the first foot member near a metatarsal region of the foot member.

As shown in FIG. 6, the prosthetic foot 50 and other prosthetic foot examples disclosed herein, for example, the prosthetic foot 10, can combine the use of several pivot points through the shape and parts used in the prosthetic foot. A first pivot point (Point 1 in FIG. 6) can be located at the toe section. As shown in FIGS. 5A-B and 6, the first foot member 500 can include a small bend 509 in the distal section 504. The bend 509 may be at a metatarsal section of the distal section 504. The bend 509 can form the first pivot point P1. In some embodiments, the toe section can be a drop toe section as described above. With continued reference to FIG. 6, at Point 1, the prosthetic foot can plantarflex and dorsiflex with relatively lower loads. The prosthetic foot 50 can bend around the metatarsal joint at Point 1. The bending at Point 1 can influence the toe push-off force of the prosthetic foot 50. By configuring the shape and layup of the bend 509 appropriately, an increased toe push-off can be created. A foot member that does not include such a bend at the metatarsal section or a drop toe section may not bend around a specific point in the toe region of the foot member and the foot member tends to bend along the enter length of the foot member when under a load, particularly a relatively lower load.

For higher activities or for certain layup profiles, a toe foot member that extends over at least the toe region of the prosthetic foot over the bend 509 can be added to cause the toe region to stiffen up or reduce the range of bending about Point 1. The toe foot member can be connected at the toe region to the first foot member 500 (for example, near the distal end 504 of the first foot member 500) so that the first foot member 500 can contact the second foot member 510 at a preferred bending angle. Alternatively, the toe foot member can be connected to the first foot member 500 further away from the distal end of the first foot member (for example, near a metatarsal region of the first foot member) and contact the toe region of the first foot member 500 at a predetermined bending angle. For both options, the length of the toe foot member can vary. An example toe foot member 1360 is shown in FIG. 11.

Figure 11:
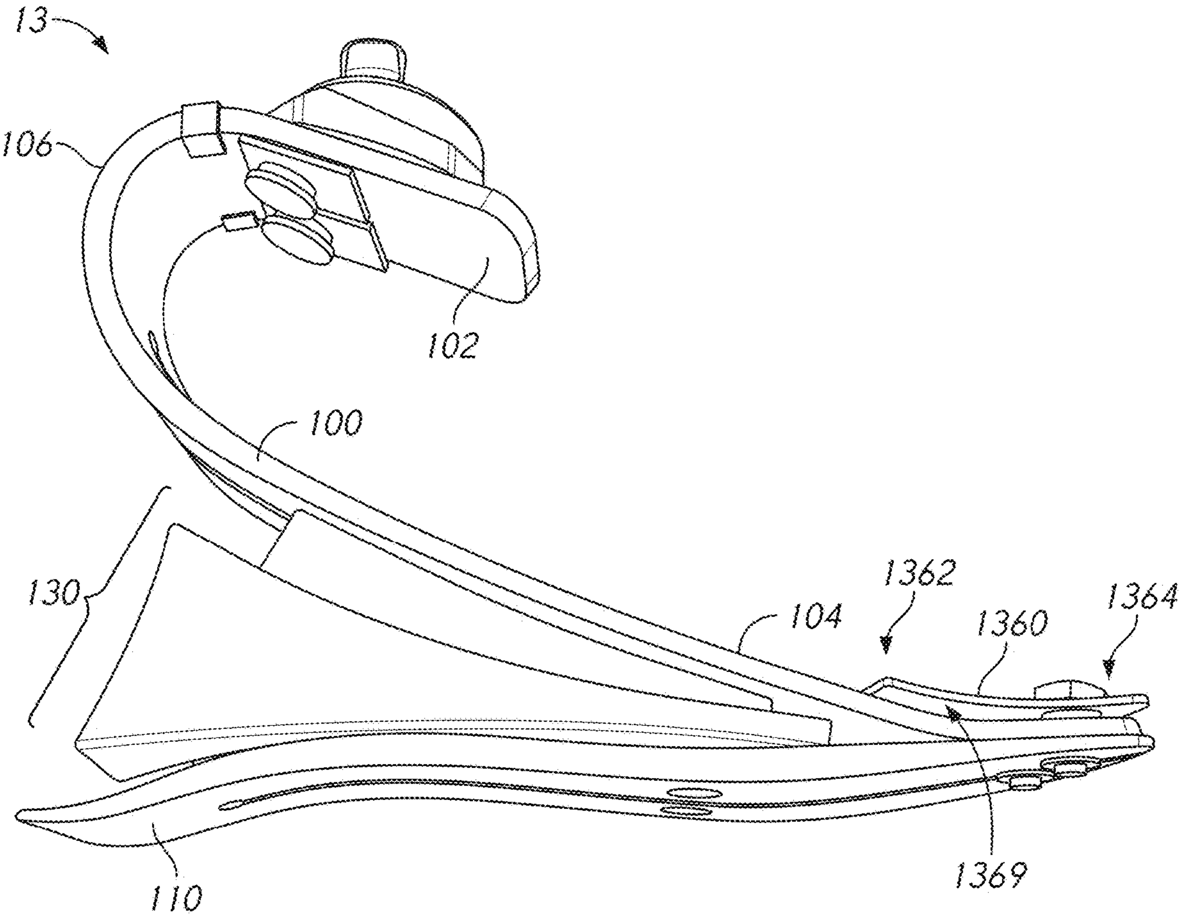
FIG. 11 illustrates another example prosthetic foot designed for multiple activity levels. 4B

When the foot member 1360 is relatively short such as shown in FIG. 11, the prosthetic foot can additionally include another foot member coupled to a proximal end of the first foot member. This foot member can have any of the features of the third foot member 160 of FIGS. 4A-B and 7A or the third foot member 560 of FIG. 5B described above.

When compressing the resilient member disclosed herein, for example, the resilient member 130, 230, 330, 530, the first foot member can be pushed in plantarflexion around a second pivot point (Point 2 in FIG. 6). With relatively higher loading and when the toe section is extended, the first foot member (with a taper as shown in FIG. 6 or with a reverse taper, which will be described in greater detail below) can flex around a third pivot point (Point 3 in FIG. 6).

Figure 7A:
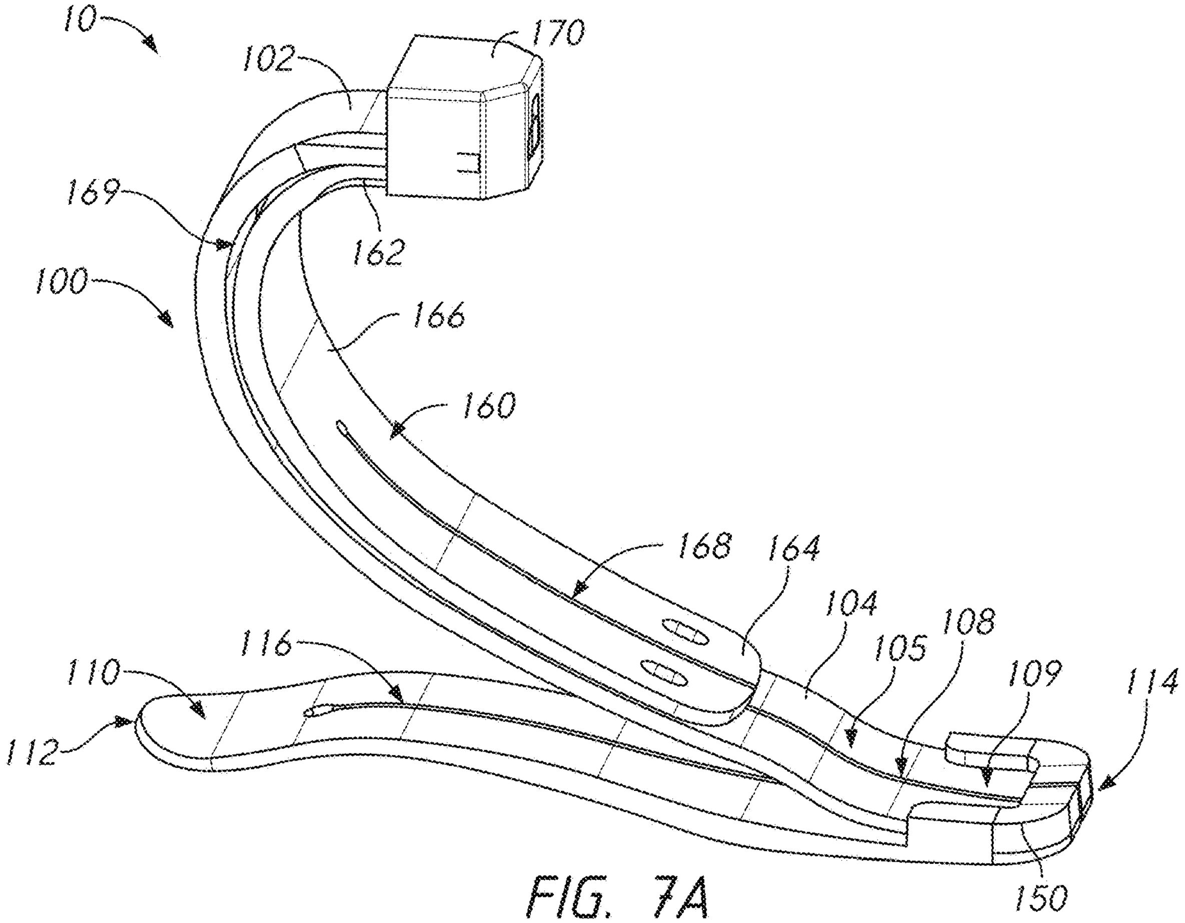
FIG. 7A illustrates a perspective view of an assembled example mechanical prosthetic foot designed for multiple activity levels.
Figure 7B:
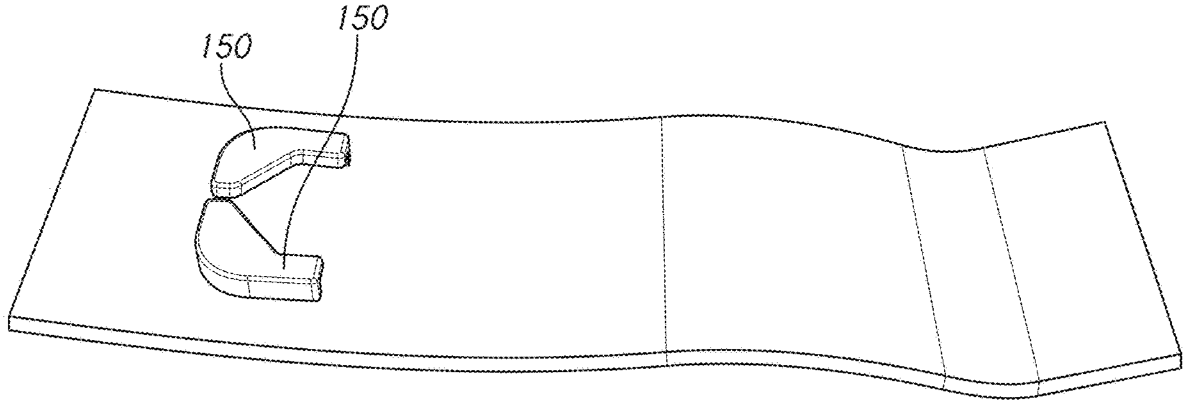
FIG. 7B illustrates an example blank carbon fiber plate for making a second foot member of the mechanical prosthetic foot disclosed herein.
Figure 7C:
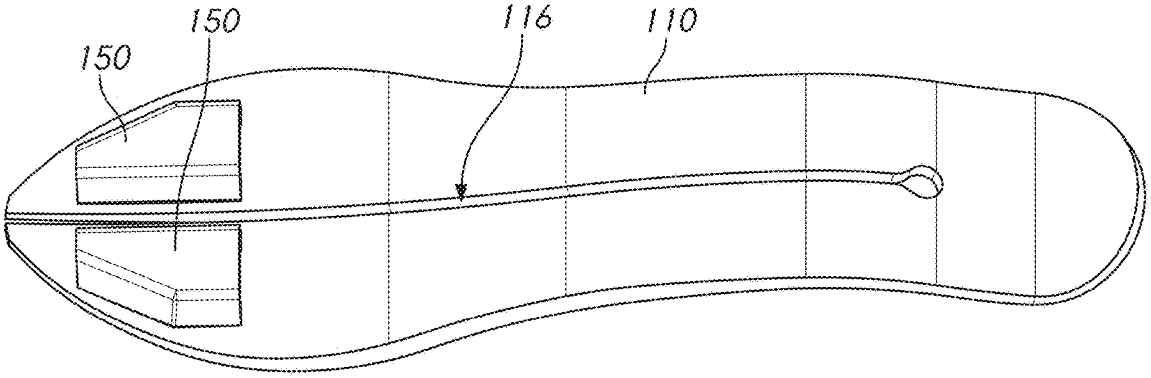
FIG. 7C illustrates an example second foot member of the mechanical prosthetic foot disclosed herein.

As shown in FIG. 7A, the second foot member 110 of the prosthetic foot 10 can include an attachment 150 for coupling with at least a portion of the vertically offset toe section 109 of the first foot member 100. The attachment 150 can be at or near the toe end 114 of the second foot member 110. In some embodiments such as shown in FIG. 7A, a distal edge of the attachment 150 can align with the toe end 114 of the second foot member 110. In some embodiments, such as shown in FIG. 7C, a distal edge of the attachment 150 can be proximal of the toe end 114 of the second foot member 110. The outer shape of the attachment 150 can be varied, with FIGS. 7A-7C each illustrating an example shape of the attachment 150. In some embodiments, such as shown in FIG. 7C, the attachment 150 can include a first part and a second part that are spaced apart and located on two segments of the second foot member 110 separated by a slot 116 in the second foot member 110. In some embodiments, such as shown in FIG. 7A, the attachment 150 can be bisected into two parts by the slot 116. In some embodiments, the attachment 150 can be molded onto an upper or top surface of the second foot member 110. The attachment 150 can include a rearward facing cavity for receiving a portion of the distal section 104 of the first foot member 100, for example, at least a portion of the vertically offset toe section 109. In one example, the attachment 150 at least partially defines a bracket that extends over at least a portion of the vertically offset toe section 109. Once received in the cavity, the at least a portion of the distal section 104 of the first foot member 100 can be glued to the second foot member 110 using adhesives. In some embodiments, such as shown in FIG. 1, the attachment 150 can include a slot so that the distal end 104*a* of the first foot member 100 (for example, at least a portion of the vertically offset toe section 109) extends, through the slot, distally of the distal edge of the attachment 150. In another embodiment, such as shown in FIG. 13, a distal edge of the attachment 1350 can define a toe end of the foot 1300 such that no foot member extends distally of the distal edge of the attachment 1350. In some embodiments, the attachment 150 can be molded onto an upper or top surface of the first foot member 100 for connection with a third foot member, which will be described below.

Alternatively, as shown in FIG. 4A, the first and second foot members 100, 110 can be coupled together using fasteners 152 near the distal end 104*a* of the first foot member 100 and the toe end 114 of the second foot member 110. When the fasteners 152 are tightened, the first and second foot members 100, 110 can move together. When the fasteners 152 are loosened and/or removed, the first and second foot members 100, 110 can move independently, resulting in a softer prosthetic foot.

Examples Third Foot Member of a Prosthetic Foot

In some embodiments, such as shown in FIG. 5B, the prosthetic foot 50 can include a third foot member 560. The third foot member 560 can be located more anterior or forward than the first foot member 500. Similar to the first foot member 500, the third foot member 560 can have a proximal section 562 coupled to the adapter 570. The proximal section 562 can be angle downward in some embodiments, similar to the proximal section 502 of the first foot member 500. The third foot member 500 can include a curved section 566, which can be generally forwardly-facing concave so that the third foot member 560 in the illustrated embodiment is generally C-shaped or any other suitable shapes. The curved section 566 can terminate at a distal end 564 of the third foot member 560. In the illustrated embodiment, the distal end 564 of the third foot member 560 can be more proximal than the distal section 504 of the first foot member. In other embodiments, the third foot member 560 can have different lengths so that the distal end 564 can terminate more proximally or more distally than as shown in FIG. 5B.

In some embodiments, when the prosthetic foot is at rest, the curved section 566 of the third foot member 560 can be spaced away from the curved section 506 of the first foot member 500 by a gap 569. During ambulation, the gap 569 can decrease till the first foot member 500 and the third foot member 560 come into contact, thereby increasing the stiffness of the prosthetic foot 50. In some embodiments, the third foot member 560 can have an effect on the stiffness of the prosthetic foot 50 when flexing around a pivot point shown as Point 3 in FIG. 6. Depending on the size of the gap 569 and/or the shape of the third foot member 560, the stiffness of the prosthetic foot when flexing around Point 3 can be greater in mid stance or toe off. The timing of when the stiffness of the prosthetic foot 50 increases can depend on, for example, when the first foot member 500 and the third foot member 560 come into contact. The amount of increase in stiffness can depend on, for example, the extent of contact between the first foot member 500 and the third foot member 560 and/or the stiffness of the third foot member 560.

In some embodiments, the prosthetic foot 50 can include more than one foot member located more anterior or forward than the first foot member 500. The foot members that are more anterior or forward than the first foot member 500 can have different lengths and therefore act at different loading conditions to vary the stiffness of the prosthetic foot 50.

In some embodiments, such as shown in FIGS. 4A-B and 7A, the prosthetic foot 10 disclosed herein (or any other prosthetic foot member disclosed herein, such as the prosthetic foot 50 shown in FIGS. 5A, -5C, and 6) can have a third foot member 160. The third foot member 160 can be located more anterior or forward than the first foot member 100. The third foot member 160 can extend from a proximal section 162 to a distal section 164. The proximal section 162 can extend to a proximal end. At least a portion of the proximal section 162 closer to the proximal end of the third foot member 160 can be coupled to the adapter 170. The distal section 164 can extend to a distal end. The distal end of the third foot member 160 is proximal to the distal end 104*a* of the first foot member 100 and can be proximal to the toe portion of the foot. In the illustrated embodiment, the distal end of the third foot member 160 is proximal to the segment 105 of downward curvature of the first foot member 100. In another embodiment, the distal end of the third foot member 160 can extend up to the toe portion of the prosthetic foot 10, for example, up to the distal end 104*a* of the first foot member 100 or the toe end 114 of the second foot member 110. In some embodiments, the distal end of the third foot member 160 can extend along the proximal section 103 and terminate at or near a proximal end of the curved section 106. In some embodiments, the distal end of the third foot member 160 can terminate at or near (for example, slightly proximal or distal to) a bend (such as the bend 509 in FIG. 5A) in a metatarsal section of the first foot member.

In the illustrated embodiment, the proximal section 162 can be generally horizontally oriented. The third foot member 160 can have a curved section 166 between the proximal section 162 and the distal section 164. The curved section 166 can be generally forwardly-facing concave. The distal section 164 can extend forwardly and downwardly from the curved section 166. In the illustrated embodiment, the third foot member 160 is generally C-shaped. In some embodiments, the curved section 166 and/or the proximal section 162 can be generally at a location of a natural human ankle. In some embodiments, the distal end 164 of the third foot member 160 can be connected to the first foot member 100, for example, via bolts through openings 165 near the distal end 164 of the third foot member 160, a quick connection adapter, or otherwise.

In some embodiments, when the prosthetic foot 10 is at rest, the first foot member 100 and the third foot member 160 can be separated by a gap 169 (see FIG. 7A) that extends between the proximal and distal ends of the first foot member 100 and the third foot member 160. A width of the gap 169 can gradually increase from the proximal ends toward the distal ends of the first foot member 100 and the third foot member 160 when the foot 10 is at rest on a flat surface. During ambulation, the width of the gap 169 gradually decreases as the prosthetic foot 10 transitions from heel-strike to toe-off. In dorsiflexion, as the first foot member 100 and the third foot member 160 come into contact, the stiffness of the prosthetic foot 10 increases progressively, advantageously allowing for greater energy storage during mid-stance and gradual stiffening of the foot 10 relative to the load amount placed on the foot 10. The stored energy is then released during toe-off to help propel the user forward. The third foot member 160 such as shown in FIGS. 4A-4B and 7A can additionally allow for a different stiffness of the foot 10 during plantarflexion compared to the stiffness during dorsiflexion. This is because the gap 169 between the first foot member 100 and the third foot member 160 remain open during plantarflexion. The third foot member 160 can also additionally provide an end stop of the bending of the first foot member 100 during higher impact activities. In some embodiments, the prosthetic foot can include more than one foot member (for example, two, three, or more) that is located anterior to the first foot member 100.

The prosthetic foot 10 may include a spacer material in the gap 169, such as a spacer material 167 in FIG. 4A. The spacer material can be configured to provide springlike characteristics, such as PU, TPU, EVA or 3D printed grid structures. In some embodiments, the stiffness of foot can change due to the spacer material by between about 5% to about 20%, by shifting the spacer material more inward or more outward, and/or by removing the spacer material completely from the prosthetic foot. The location and/or the width of the spacer material can affect the stiffness of the heel and toe. In some embodiments, the user may slide the spacer material back and forth along the gap 169 in order to adjust the stiffness of the foot, for example, to adjust for a lower impact or higher impact activity. Alternatively, the point of contact between the first and third foot members can be varied with other mechanical fasteners that connect the third foot member to the first foot member. In some embodiments, a screw can be used to bolt the first and third foot members together to cause the first and third members to move together. Loosening and/or removing the screw can allow the first and third foot members to move independently of each other, and thus becoming softer.

Alternatively, the prosthetic foot disclosed herein can include a third foot member than extends from a toe portion or distal portion of the prosthetic foot toward an ankle or proximal portion of the prosthetic foot. In some embodiments, such a third foot member can stiffen a toe portion with a vertical offset (also referred to as a "drop toe section") as disclosed herein. The faster the user walks, the less the user places a load on the drop toe section and the more the user places the load on the remainder of the first foot member.

Other Example Features of a Prosthetic Foot

In the illustrated embodiments, such as shown in FIGS. 1, 2B, 2C, and 3-7A, the first foot member 100 can include a taper so that a thickness of the first foot member 100 is the greatest in the curved section 106, and gradually decreases toward the distal section 104. The gradual decrease in thickness can extend to the distal end 104*a*. As described above, the foot members can include a composite laminate material. The thickness and the taper of the first foot member 100 can be varied by the number of layups of the laminate. In other embodiments, the taper can be reversed (see, for example, the first foot member 400 in FIGS. 8A-8C) in the first foot member compared to the taper shown in FIGS. 1, 2B, 2C, and 3-7A. For example, the first foot member can be the thinnest in the proximal section 102 and the thickness can gradually increase toward the curved section 106 and/or the distal section 104. The reverse taper can move the center of rotation of the first foot member more proximally. The more proximal center of rotation can be closer to the ankle joint.

As shown in FIG. 7A, the first foot member 100 can include multiple elongate segments that can flex independently relative to each other. The first foot member 100 can include two elongate segments that are separated from each other by a split (or slot) 108 that extends along a length between the distal end 104*a* and the proximal end 102*a* of the first foot member 100. As shown in FIG. 7A, the second foot member 100 can include multiple elongate segments that can flex independently relative to each other. In the illustrated embodiment, the second foot member 110 can include two elongate segments that are separated from each other by the split (or slot) 116 that extends along a length between the distal end 114 and the proximal end 112 of the second foot member 110. As shown in FIG. 7A, the third foot member 160 can include multiple elongate segments that can flex independently relative to each other. In the illustrated embodiment, the third foot member 160 can include two elongate segments that are separated from each other by a split (or slot) 168 that extends along a length between the distal end and the proximal end of the third foot member 160. In some embodiments, the split 108 in the first foot member 100, the split 116 in the second foot member 110, and the split 168 in the third foot member 160 can align with one another.

Additional Example Prosthetic Foot

FIGS. 8A-11 illustrate additional example prosthetic feet that are variations of the prosthetic foot 10, 50. Any of the features of the prosthetic foot examples in FIGS. 8A-11 can be incorporated into the prosthetic foot 10, 50 and any of the features of the prosthetic foot 10, 50 can be incorporated into the prosthetic foot examples in FIG. 8A-11. Features of the prosthetic foot examples in FIG. 8A-11 can also be incorporated into one another.

Figure 8A:
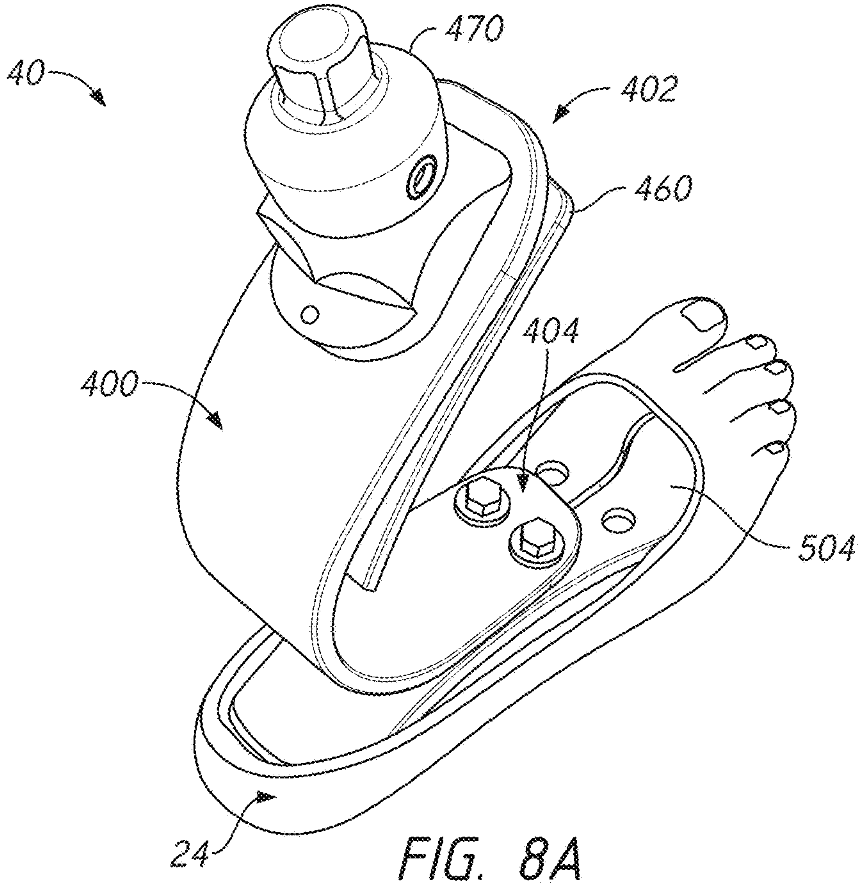
FIG. 8A illustrates another example mechanical prosthetic foot designed for multiple activity levels inside a foot cover.
Figure 8B:
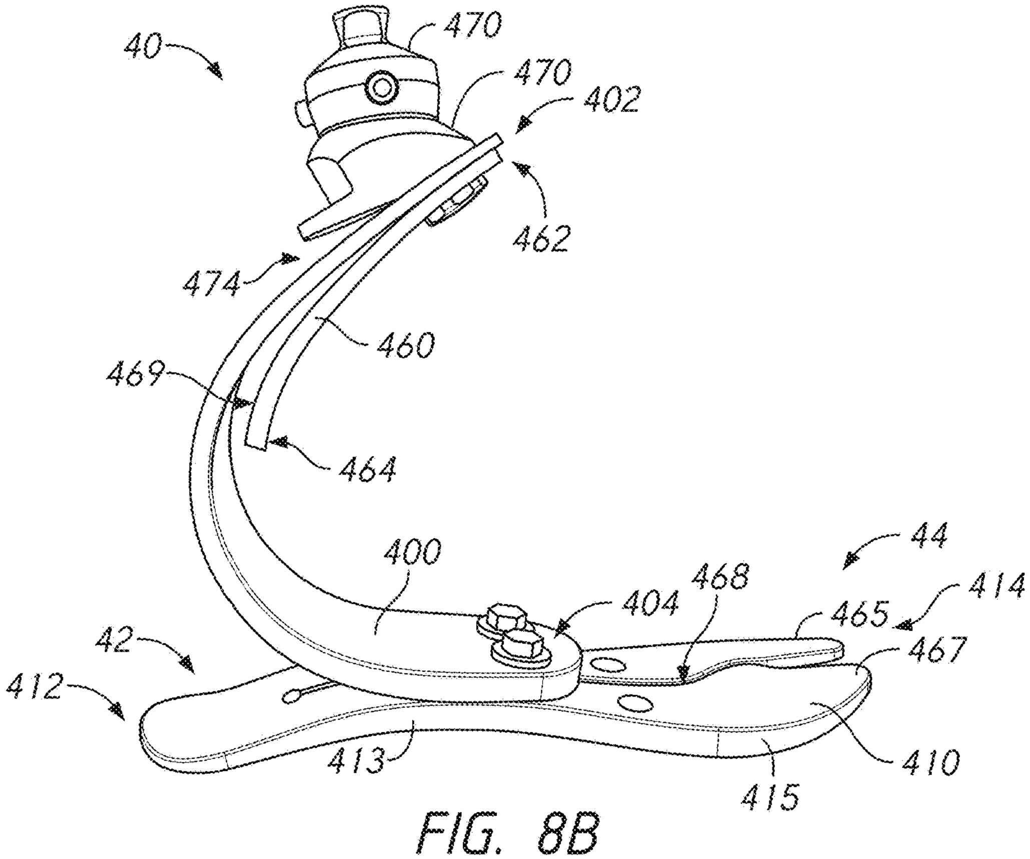
FIG. 8B illustrates the mechanical prosthetic foot of FIG. 8A without the foot cover.
Figure 8C:
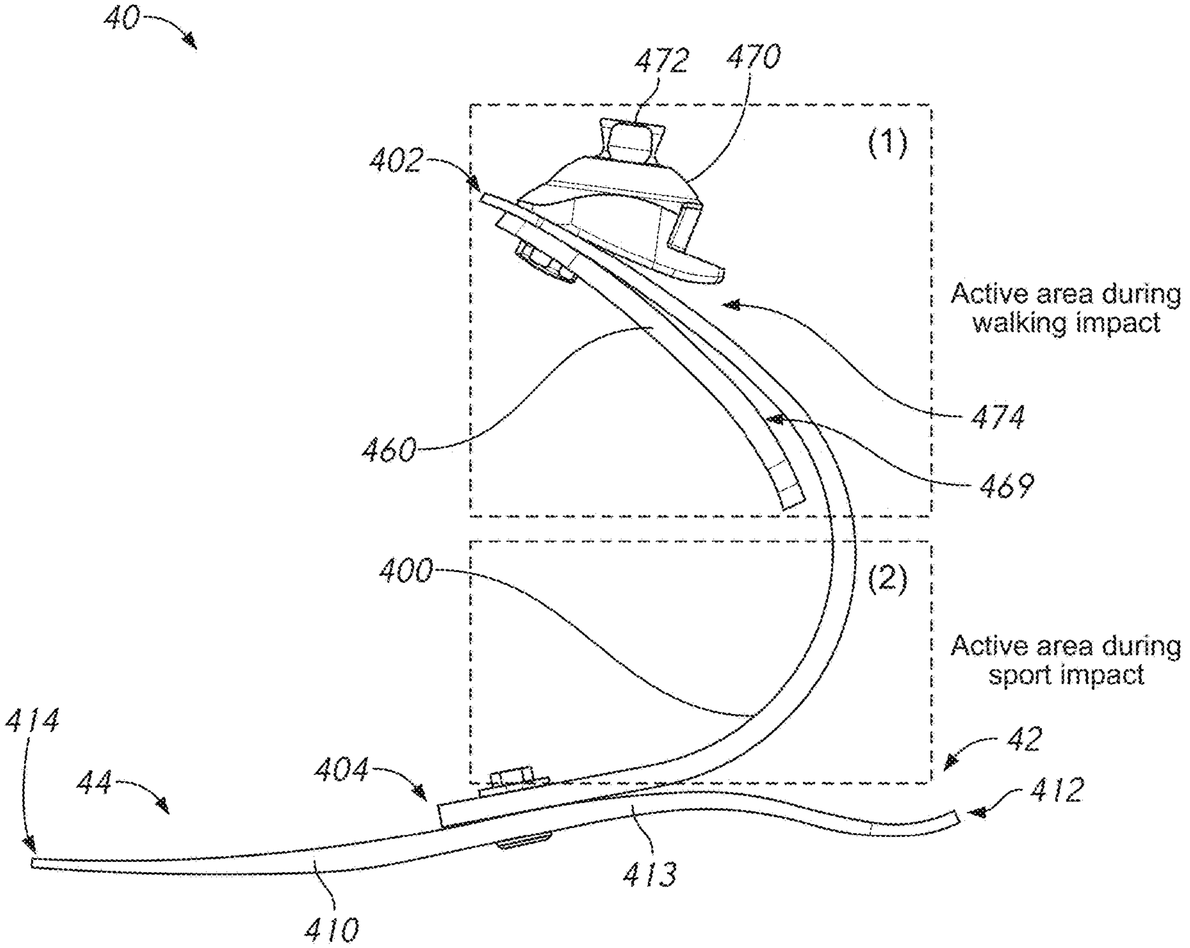
FIG. 8C illustrates active areas of the prosthetic foot of FIG. 8A for different activity levels.

FIGS. 8A-8C illustrate a prosthetic foot 40. The prosthetic foot 40 can have any of the features of the prosthetic foot 10, 50, with the differences noted in the description of FIGS. 8A-8C. As shown in FIGS. 8A-8C, the prosthetic foot 40 can include a first foot member 400 that extends from a proximal end 402 to a distal end 404. The first foot member 400 can be generally curved from the proximal end 402 to the distal end 404. The first foot member 400 can be generally C-shaped. A portion of the first foot member 400 closer to the proximal end 402 can be coupled to an adapter 470 such that a posterior portion of the adapter 470 is spaced from the first foot member 400 by a gap 474 that can vary in size during ambulation. The gap 474 can close completely to stiffen up the first foot member 400 (for example, by shifting the bending point, shortening the lever arm, and the like). The specific angle of the gap 474 can be dependent on the stiffness of the first foot member 400 and its tapering of the layers.

The prosthetic foot 40 can include a second foot member 410. The second foot member 410 can have any of the features of the second foot member 110 described above. The second foot member 410 can be located below the first foot member 400 when the foot 40 is in a neutral or resting position on a flat surface. The second foot member 410 can extend from a heel end 412 to a toe end 414. The heel end 412 can define a heel end 42 of the prosthetic foot 40. The toe end 414 can define a toe end 44 of the prosthetic foot 40. The second foot member 410 can include an arch region 413 between the heel end 412 and the toe end 414. For example, the arch region 113 can be at approximately the location of an arch of a natural human foot. The second foot member 410 can include a forefoot region 415 distal to the arch region 413 or between the arch region 413 and the toe end 414. The second foot member 410 can be curved upward in the arch region 413 relative to a remainder of the second foot member 410.

The distal end 404 of the first foot member 400 can terminate proximal to the toe end 414 of the second foot member 410. The distal end 404 of the first foot member 400 can terminate distal to the arch region 413 of the second foot member 410. The distal end 404 of the first foot member 400 can terminate near or proximal to the forefoot region 415 of the second foot member 410. The first foot member 400 can be coupled (for example, fastened) to the second foot member 410 near the distal end 404 of the first foot member 400.

The prosthetic foot 40 can include a third foot member 460. The third foot member 460 can be located more anterior or forward than the first foot member 400. The third foot member 460 can extend from a proximal end 462 to a distal end 464.

In some embodiments, when the prosthetic foot 40 is at rest, the first foot member 100 and the third foot member 160 can be separated by a gap 469 that extends between the proximal and distal ends 462, 464 of the third foot member 460. A width of the gap 469 can gradually increase from the proximal end 462 toward the distal end 464 of the third foot member 460 when the foot 40 is at rest on a flat surface. During ambulation, the width of the gap 469 gradually decreases as the prosthetic foot 40 transitions from heel-strike to toe-off as described above with reference to the prosthetic foot 10. The third foot member 460 such as shown in FIGS. 8A-8C can allow for a different stiffness of the foot 40 during plantarflexion compared to the stiffness during dorsiflexion.

The first foot member 400 and/or the third foot member 460 can include a taper so that a thickness of the first foot member 400 and/or the third foot member 460 is the greatest at the distal end 404, 464, and gradually decreases toward the proximal end 402, 462.

As shown in FIGS. 8A and 8B, the third foot member 460 can include multiple elongate segments that can flex independently relative to each other. In the illustrated embodiment, the third foot member 460 can include two elongate segments that are separated from each other by a split (or slot) 468 that extends along a length between the distal end 462 and the proximal end 464 of the third foot member 460. The split 468 may include a turn medially near the forefoot region 415, separating a toe region of the second foot member 410 into two segments with unequal width. A medial segment 465 can include a big-toe like appearance. The medial segment 465 can be separated from a lateral segment 467 by a generally U-shaped cutout portion. In the illustrated embodiment, the first and/or third foot members 400, 460 may not include a lengthwise split.

FIG. 8C illustrates how the prosthetic foot 40 includes two stiffness areas and/or accommodate different activity levels. A first stiffness area, Area (1) in FIG. 8C, can be the active area when the prosthetic foot 40 is experiencing impact from walking (or a lower impact). Area (1) can extend from the proximal end 402 of the first foot member toward the distal 404. Area (1) can terminate generally at the distal end 464 of the third foot member 460. A second stiffness area, Area (2) in FIG. 8C, can be the active area when the prosthetic foot 40 is experiencing impact from running or sports activities (or a higher impact). In some embodiments, the loading on the foot 40 changes from a vertical pylon movement during walking (or a lower impact activity) to a horizontal generally C-shaped loading during running (or a higher impact activity).

During walking (or a lower impact activity), the taper of the first foot member 400 allows a portion of the first foot member 400 nearer to the proximal end 402 to move and contact the third foot member 460. Being thinner near the proximal end 402, the portion of the first foot member 400 near the proximal end 402 (also an upper portion of the first member 400 when the foot 40 is resting on a flat surface) can move more easily under a lower impact (such as during walking) than the thicker portion of the first foot member 400 near the distal end 404 (also a lower portion of the first foot member 400 when the foot 40 is resting on a flat surface).

During a higher impact activity, the active or working area of the foot 40 is shifted toward the thicker portion (or the lower portion) of the first foot member 400. Under the higher impact, the third foot member 460 can substantially entirely contact the first foot member 400 throughout the higher impact activity, thereby increasing the stiffness of Area (1). The increased stiffness in Area (1) can shift a bending area of the first foot member 400 toward Area (2).

In some embodiments, the load line shifts along the first foot member 400 when the user switches from a lower impact activity to a higher impact activity. For example, the load line can be at about ⅓ of a length of the first foot member 400 from the proximal end 402 under a lower impact. The load line can be shifted to at about half the length of the first foot member 400 from the proximal end 404 under a higher impact. The shift in the load line can aid the foot 40 to be more suitable for running or other higher impact activity, when it is more desirable for the load line to be closer to the toe region of the first foot member 400.

Figure 9:
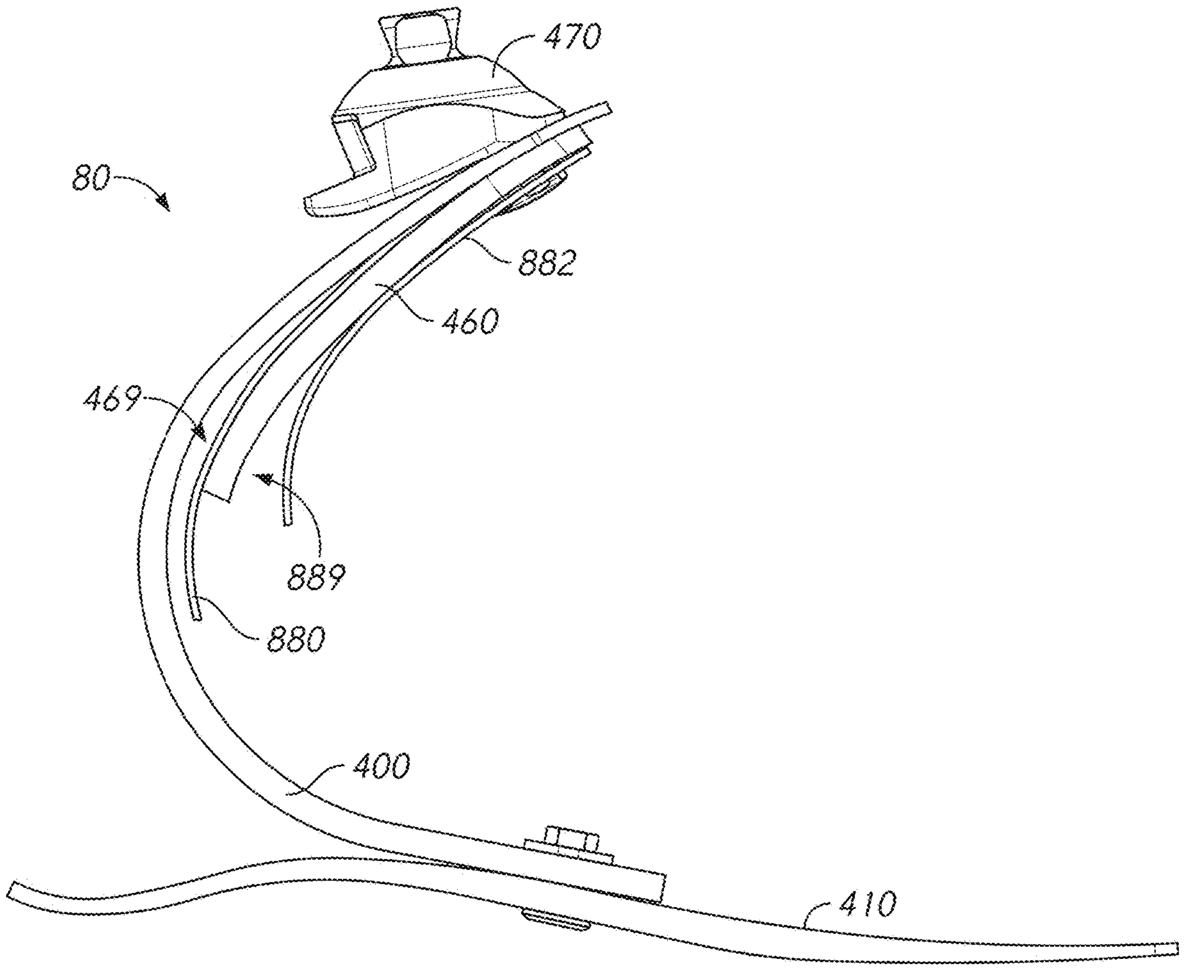
FIG. 9 illustrates another variation of the prosthetic foot of FIG. 8A.

FIG. 9 illustrates a prosthetic foot 80 that is a variation of the prosthetic foot 40. Any of the features of the prosthetic foot 80 can be incorporated into the prosthetic foot 40 and the prosthetic foot 80 can include any of the features of the prosthetic foot 40, with the difference noted in the description of FIG. 9. In addition to the first, second, and third foot members 400, 410, 460, the prosthetic foot 80 can include a first liner 880 and a second liner 882. The first and/or second liners 880, 882 can reduce or remove noise and improve mating of parts of the prosthetic foot 80. The first liner 880 can be located between the first foot member 400 and third foot member 460. The second liner 882 can be more anterior than the third foot member 460. The first and second liners 880, 882 can be on opposite sides of the third foot member 460. The first and second liners 880, 882 can be coupled to the adapter 470 at proximal ends of the first and second liners 880, 882. When the foot 80 is resting on a flat surface, the first liner 880 can contact the third foot member 460, leaving the gap 469 open. When the foot 80 is resting on a flat surface, a gap 889 can exist between the second liner 882 and the third foot member 460. Similar to the gap 469, the gap 889 can gradually decrease during dorsiflexion of the foot 80 as described above with reference to the prosthetic foot 10.

Figure 10A:
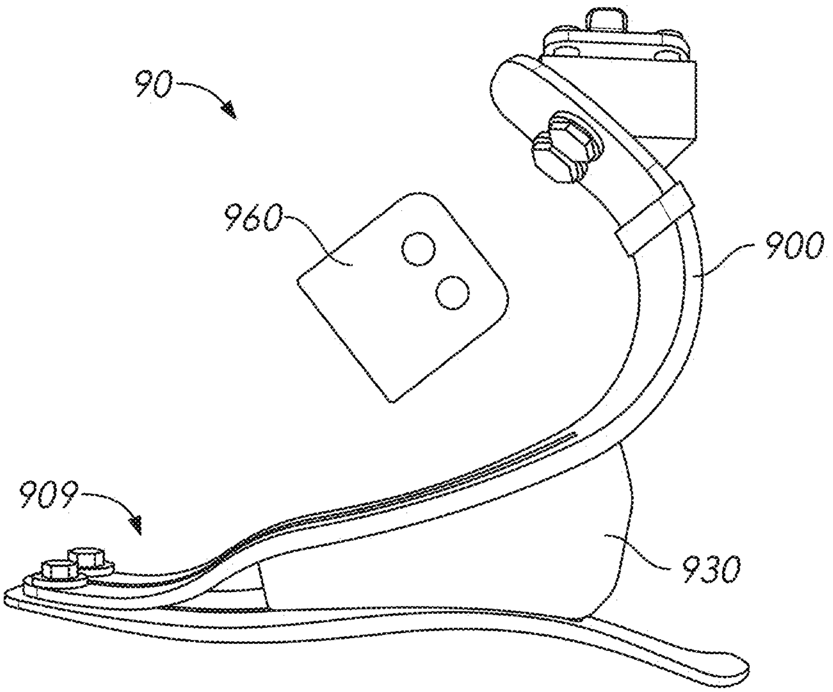
FIGS. 10A and 10B illustrate another example mechanical prosthetic foot designed for multiple activity levels.
Figure 10B:
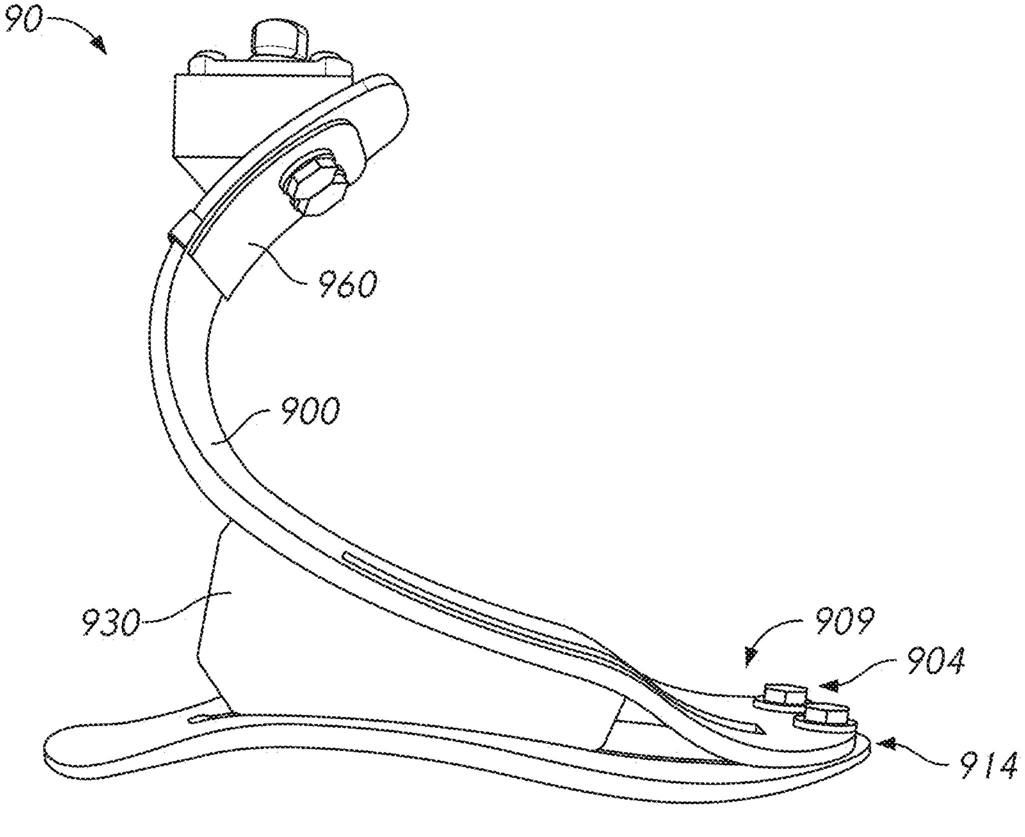

FIGS. 10A and 10B illustrate a prosthetic foot 90. The prosthetic foot 90 can include a combination of features of the prosthetic foot 10, the prosthetic foot 50, and the prosthetic foot 40, 60, 80. For example, the prosthetic foot 90 can include a resilient member 930 that can have any of the features of the resilient member 130, 230, 330, 530. The resilient member 930 can allow for a greater degree of plantarflexion upon heel strike. As another example, the prosthetic foot 90 can include a drop toe section 909 in the first foot member 900, similar to the drop toe section 109 in the first foot member 100 and the first foot member 500. Additionally, the first foot member 900 of the prosthetic foot 90 can have a combination of features of the first foot member 100, 400, 500. The first foot member 900 can be generally curved between a proximal end 902 and a distal end 904. The prosthetic foot 90 can have a center of rotation that can be higher and more rearward, similar to the center of rotation of the prosthetic foot 40, 60, 80, due to the shape of the first foot member 900 near the proximal end 902. The higher and more rearward center of rotation can make the prosthetic foot 90 more adapted for running or other higher impact activity levels. The distal end 904 can terminate at a region of a natural human toe. The first and second foot members 900, 910 can be coupled (for example, fastened) at the distal end 904 of the first foot member and a toe end 914 of the second foot member 910. The prosthetic foot 90 can further include a third foot member 960 coupled near a proximal end of the first foot member 900. The third foot member 960 can include stiffness of a proximal section of the first foot member 900, for example, during higher impact activities.

FIG. 11 illustrates an example prosthetic foot 13. The prosthetic foot 13 can be a variation of the prosthetic foot 10 described above. The prosthetic foot 13 can include any of the features of the prosthetic foot 10, with the differences noted in the description of FIG. 11. Optionally, the prosthetic foot 13 can include any of the features of the other prosthetic foot examples disclosed herein. Any of the prosthetic foot examples disclosed herein can incorporate features of the prosthetic foot 13.

As shown in FIG. 11, a third foot member 1360 of the prosthetic foot 13 can be connected to the first and second foot members 100, 110 at a toe end 1364 of the third foot member 1360 As described above, for higher activities or for certain layup profiles, the third foot member can cause the toe region of the foot 13 to stiffen up or reduce the range of bending about a pivot point in the toe region. The first, second, and third foot members 100, 110, 1360 can be coupled by the attachment 150. The third foot member 1360 can extend from the toe end 1364 to a proximal end 1362. The third foot member 1360 can be coupled to the first foot member 100 near the distal end of the first foot member 100. Alternatively, the third foot member 1360 can be coupled to the first foot member 100 further away from the distal end of the first foot member 100 (for example, near a metatarsal region of the first foot member).

The proximal end 1362 can be more distal than the proximal end 102 of the first foot member 100. At least a portion of the third foot member 1360 is separated from the first foot member 100 by the gap 1369. The gap 1369 can close during dorsiflexion of the foot 13. The third foot member 1360 can restrict movement of the first foot member 100 during dorsiflexion of the foot 13. As discussed above with reference to FIG. 6, the third foot member 1360 can increase stiffness of a metatarsal region or the distal section 104 of the first foot member 100 during dorsiflexion. The length of the third foot member 1360 can vary. As shown in FIG. 11, the third foot member 1360 can extend from a toe end of the foot 13 to a location generally corresponding to a metatarsal location. In other embodiments, the third foot member 1360 can extend more proximally than the metatarsal region. When the third foot member 1360 is relatively short such as shown in FIG. 11, the prosthetic foot 13 can additionally include a fourth foot member. In some embodiments, the fourth foot member can have any of the features of the third foot member 160 of FIG. 4A described above.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise. Additionally, as used herein, "gradually" has its ordinary meaning (e.g., differs from a non-continuous, such as a step-like, change).

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A prosthetic foot configured to allow a user to engage in different activity levels, the foot comprising:

a first foot member, the first foot member including a proximal end and a distal end, the proximal end configured to couple to an adapter, wherein the adapter is configured to couple the prosthetic foot to another prosthetic component, wherein the first foot member includes a proximal section extending from the proximal end to a curved portion, and a distal section extending between the curved portion and the proximal and distal end, the distal section extending forward and downward from the curved portion, and wherein the proximal portion of the first foot member between the proximal end and the curved portion is bent downward toward the distal end of the first foot member;

a second foot member below the first foot member when the prosthetic foot is resting on a flat surface, the second foot member including a heel end and a toe end, the heel end defining a heel end of the prosthetic foot and the toe end defining a toe end of the prosthetic foot;

and a resilient member located between the first and second foot members, the resilient member being rearward of a coupling location of the first and second foot members, the resilient member comprising an upper resilient component and a lower resilient component, wherein the lower resilient component comprises a cut-out portion extending from a proximal, upper end of the lower resilient component and forming a slot between the upper resilient component and the lower resilient component, wherein the cut-out portion is oriented such that a height of the cut-out portion is highest toward the heel end of the prosthetic foot and decreases toward the toe end of the prosthetic foot.

2. The prosthetic foot of claim 1, wherein the resilient member comprises a plurality of grooves.

3. The prosthetic foot of claim 1, wherein the resilient member is configured to push the prosthetic foot into plantarflexion and to provide vertical shock absorption upon heel strike.

4. The prosthetic foot of claim 3, wherein the resilient member is configured to push the prosthetic foot into plantarflexion of at least 8°.

5. The prosthetic foot of claim 1, wherein the first and second members are directly coupled to each other only at the coupling location.

6. The prosthetic foot of claim 5, wherein the first foot member and the second foot member are coupled by a mechanical fastener at the coupling location, and wherein the coupling location is more anterior than the adapter.

7. The prosthetic foot of claim 1, wherein the first foot member includes a toe region terminating at the distal end, at least a portion of the toe region of the first foot member being coupled to the second foot member near the toe end of the second foot member.

8. The prosthetic foot of claim 1, wherein a distance between a bottom surface of the upper resilient component and a top surface of the lower resilient component is configured to change during ambulation such that debris can be trapped between the bottom surface of the upper resilient component and the top surface of the lower resilient component.

9. A prosthetic foot configured to allow a user to engage in different activity levels, the foot comprising:

a first foot member, the first foot member including a proximal end and a distal end, the proximal end configured to couple to an adapter, wherein the adapter is configured to couple the prosthetic foot to another prosthetic component;

a second foot member below the first foot member when the prosthetic foot is resting on a flat surface, the second foot member including a heel end and a toe end, the heel end defining a heel end of the prosthetic foot and the toe end defining a toe end of the prosthetic foot;

and a resilient member located between the first and second foot members, the resilient member being rearward of a coupling location of the first and second foot members, wherein the resilient member comprises a first resilient component and a second resilient component separated from the first resilient component, an under surface of the first resilient component partially overlapping with and in contact with an upper surface of the second resilient component, the first and second resilient components shaped to form pivot points to push the prosthetic foot into plantarflexion and to provide vertical shock absorption during heel strike;

wherein the second resilient component extends proximate the distal end of the first foot member, the second resilient component providing a vertical end stop to reduce a range of bending of the first foot member during vertical impact of the prosthetic foot wherein one of the first resilient component or second resilient component comprises a cut-out portion near a proximal end of the first resilient component or second resilient component, the cut-out portion defining a slot between the first resilient component and the second resilient component.

10. The prosthetic foot of claim 9, wherein a toe region of the first foot member is vertically offset from a remainder of a distal section of the first foot member.

11. The prosthetic foot of claim 9, wherein the first foot member is generally C-shaped.

12. The prosthetic foot of claim 9, wherein the first foot member extends forward and downward from the proximal end to the distal end.

13. The prosthetic foot of claim 9, wherein the first foot member tapers toward the distal end.

14. The prosthetic foot of claim 9, further comprising a third foot member connected to the first and/or second foot members.

15. The prosthetic foot of claim 9, wherein the first and second members are directly coupled to each other only at the coupling location.

16. The prosthetic foot of claim 9, wherein the resilient member comprises three or more components.

17. The prosthetic foot of claim 9, wherein the first resilient component and the second resilient component are staggered such that a proximal end of the first resilient component extends more proximally than a proximal end of the second resilient component, and a distal end of the first resilient component terminating proximal of a distal end of the second resilient component.

18. The prosthetic foot of claim 9, wherein the first foot member includes a toe region terminating at the distal end, at least a portion of the toe region of the first foot member being coupled to the second foot member near the toe end of the second foot member.

19. The prosthetic foot of claim 9, wherein the first foot member includes a curved portion between the proximal and distal ends, and wherein a proximal portion of the first foot member between the proximal end and the curved portion is bent downward toward the distal end of the first foot member.

20. The prosthetic foot of claim 9, wherein a distance between a bottom surface of the first resilient component and a top surface of the second resilient component is configured to change during ambulation such that debris can be trapped between the bottom surface of the first resilient component and the top surface of the second resilient component.

* * * * *